(12) United States Patent
Fiebig et al.

(10) Patent No.: US 11,478,347 B2
(45) Date of Patent: Oct. 25, 2022

(54) SPHINCTER SIZING INSTRUMENT

(71) Applicant: ETHICON LLC, Guaynabo, PR (US)

(72) Inventors: Kevin M. Fiebig, Cincinnati, OH (US); Frederick E. Shelton, IV, Hillsboro, OH (US); Michael D. Cronin, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 482 days.

(21) Appl. No.: 16/221,678

(22) Filed: Dec. 17, 2018

(65) Prior Publication Data
US 2020/0188079 A1 Jun. 18, 2020

(51) Int. Cl.
A61F 2/04 (2013.01)
A61B 5/107 (2006.01)
(Continued)

(52) U.S. Cl.
CPC .............. A61F 2/04 (2013.01); A61B 5/1076 (2013.01); A61B 90/06 (2016.02);
(Continued)

(58) Field of Classification Search
CPC . A61B 5/1076; A61B 2090/061; A41F 1/002; A44D 2203/00; A45C 13/1069; A45F 5/00; A47G 1/17; A47G 2001/0672; A47G 2009/004; A47G 2023/0666; A61M 25/0127; A63H 33/046; B65G 15/58; E04B 9/248; E04B 13/0883; E04B 15/02144;
(Continued)

(56) References Cited

U.S. PATENT DOCUMENTS 5,122,136 A 6/1992 Guglielmi et al.
5,204,382 A 4/1993 Wallace et al.
(Continued)

FOREIGN PATENT DOCUMENTS

DE 3011742 A1 10/1981
EP 1547549 A2 6/2005
(Continued)

OTHER PUBLICATIONS

U.S. Appl. No. 15/908,875, entitled Laparoscopic Sizing Instrument, filed Mar. 3, 2018.
(Continued)

Primary Examiner — Daniel L Cerioni
Assistant Examiner — Raymond P Dulman
(74) Attorney, Agent, or Firm — Frost Brown Todd LLC

(57) ABSTRACT

A sphincter sizing instrument includes a body that defines a lumen and a shaft that longitudinally translates through the lumen relative to the body. The body includes opposing proximal and distal ends. The distal end includes a first magnetic coupling feature and a first mechanical coupling feature. The shaft includes opposing proximal and distal ends and a coupler coupled with the distal end. The coupler includes a second magnetic coupling feature and a second mechanical coupling feature. The second magnetic coupling feature is configured to attract and couple with the first magnetic coupling feature to form a magnetic connection. The second mechanical coupling feature is configured to couple with the first mechanical coupling feature to form a mechanical connection.

20 Claims, 14 Drawing Sheets

(51) Int. Cl.
*A61B 90/00* (2016.01)
*A61B 17/12* (2006.01)
*A61B 17/00* (2006.01)
*A61B 18/00* (2006.01)

(52) U.S. Cl.
CPC ............ *A61B 17/12099* (2013.01); *A61B 2017/00818* (2013.01); *A61B 2018/00553* (2013.01); *A61F 2002/044* (2013.01); *A61F 2210/009* (2013.01)

(58) Field of Classification Search
CPC ............ E04B 19/0472; E04B 19/086; E04F 21/1866; E04F 2201/06; F16B 2001/0035; F16C 2226/0035; F16C 2226/18
See application file for complete search history.

(56) References Cited

U.S. PATENT DOCUMENTS

| | | | |
|---|---|---|---|
| 5,509,888 A | 4/1996 | Miller | |
| 5,702,361 A | 12/1997 | Evans, II et al. | |
| 6,543,456 B1 | 4/2003 | Freeman | |
| 7,175,589 B2 | 2/2007 | Deem et al. | |
| 7,374,565 B2 | 5/2008 | Hassler, Jr. et al. | |
| 7,390,294 B2 | 6/2008 | Hassler, Jr. | |
| 7,445,010 B2 | 11/2008 | Kugler et al. | |
| 7,481,763 B2 | 1/2009 | Hassler, Jr. et al. | |
| 7,695,427 B2 | 4/2010 | Kugler et al. | |
| 7,727,141 B2 | 6/2010 | Hassler, Jr. et al. | |
| 7,879,068 B2 | 2/2011 | Dlugos et al. | |
| 8,070,670 B2 | 12/2011 | Deem et al. | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,715,157 B2 | 5/2014 | Berg et al. | |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| 10,405,865 B2 | 9/2019 | Shelton, IV et al. | |
| 2002/0116794 A1* | 8/2002 | Hoffman | A44B 5/00 24/303 |
| 2004/0267291 A1* | 12/2004 | Byrum | A61F 5/005 606/157 |
| 2005/0283235 A1 | 12/2005 | Kugler et al. | |
| 2008/0097487 A1* | 4/2008 | Pool | A61F 5/003 606/151 |
| 2008/0249404 A1* | 10/2008 | Mikkaichi | A61B 17/0625 600/437 |
| 2009/0005797 A1* | 1/2009 | Laufer | A61F 5/0086 606/157 |
| 2009/0062824 A1 | 3/2009 | Berg et al. | |
| 2011/0098731 A1 | 4/2011 | Whitbrook et al. | |
| 2014/0336696 A1 | 11/2014 | Kugler et al. | |
| 2015/0105859 A1* | 4/2015 | Frigstad | A61F 2/0036 623/14.13 |
| 2016/0373152 A1* | 12/2016 | Schmidt | F16M 13/04 |
| 2017/0055986 A1 | 3/2017 | Harris et al. | |
| 2017/0120401 A1* | 5/2017 | Fullerton | B23P 15/001 |
| 2019/0029689 A1 | 1/2019 | Shelton, IV et al. | |
| 2019/0269436 A1* | 9/2019 | Flakne | A61B 17/2909 |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |

OTHER PUBLICATIONS

U.S. Appl. No. 15/914,381, entitled "Tunable Magnetic Sphincter Augmentation Device," filed Mar. 7, 2018.
U.S. Appl. No. 15/914,407, entitled "MRI Compatible Magnetic Sphincter Augmentation Device," filed Mar. 7, 2018.

* cited by examiner

SPHINCTER SIZING INSTRUMENT

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which affects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscles of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
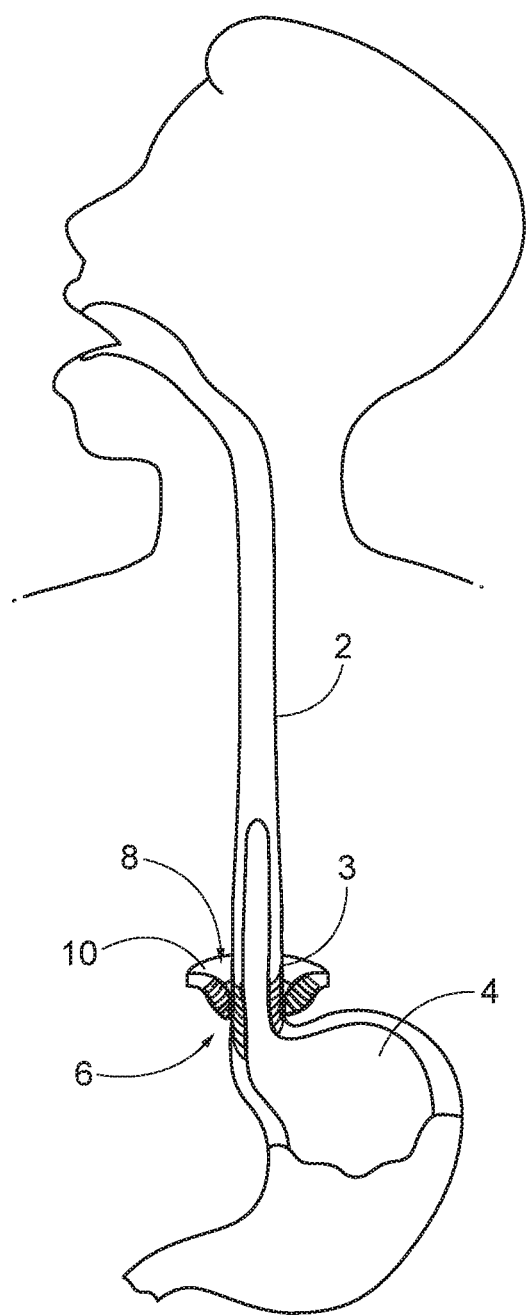
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

Figure 2:
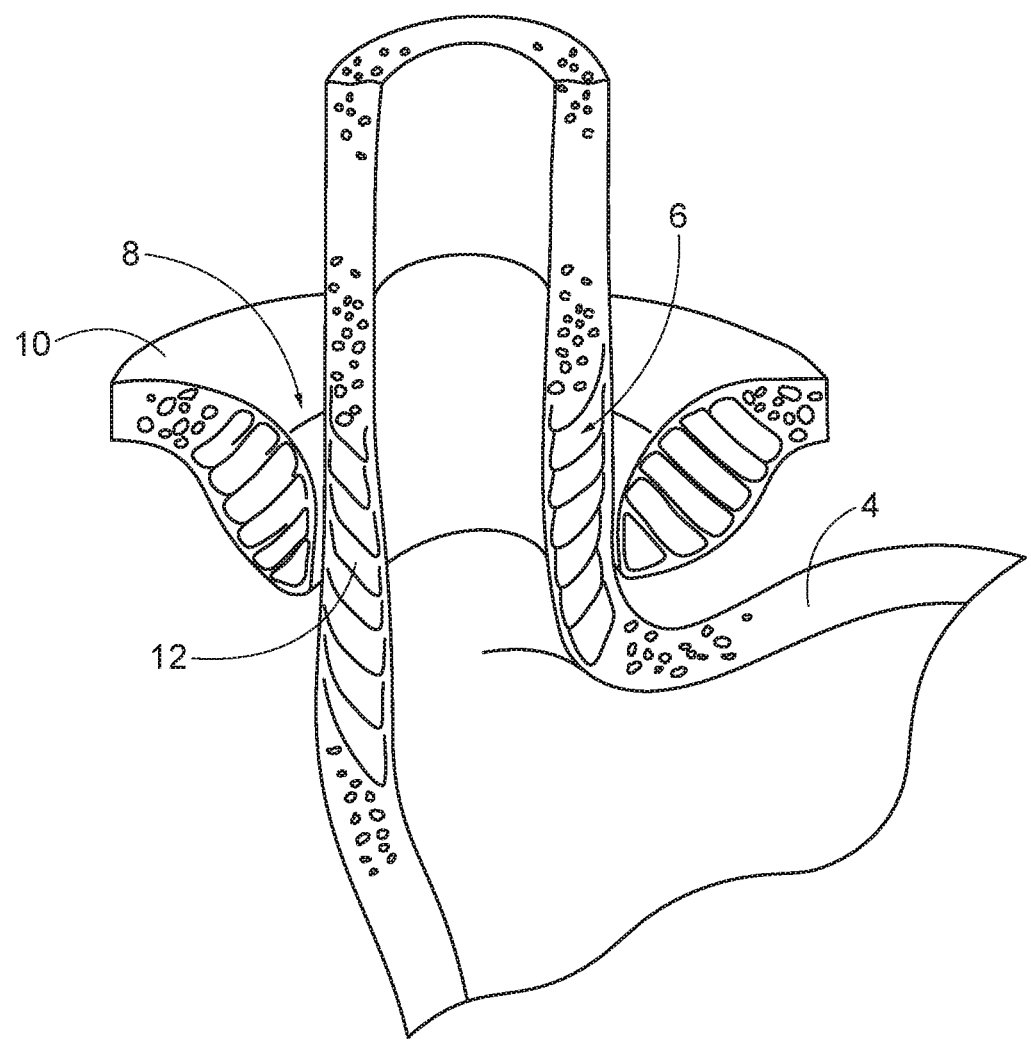
FIG. 2 depicts a cross-sectional isometric view, taken along a coronal plane of the body, of a human esophagogastric junction.

I. Overview of Exemplary Sphincter Augmentation Device and Laparoscopic Sizing Instrument A. Exemplary Sphincter Augmentation Device FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state in order to act as a valve. In other words, a healthy LES (6) may transition from the occluded state to the opened state in order to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Such an implant may include a circumferential array of magnetic elements that are magnetically attracted toward adjacent magnetic elements. Such magnetic elements may expand and contract relative to each other while encompassing the exterior of a malfunctioning LES (6). Therefore, the magnetic attraction between adjacent magnetic elements may help a malfunctioning LES (6) properly remain in an occluded state; while the ability for magnetic elements to expand and contract relative to each other may allow an LES (6) to suitably transition into the opened state. While magnetic elements are used to bias a malfunctioning LES (6) toward an occluded state while also allowing a malfunctioning LES (6) to suitably transition into an open state, any other type of biasing elements may be used as would be apparent to one having ordinary skill in the art in view of the teachings herein. Merely illustrative examples of implants that may be used to encompass the exterior of a malfunctioning LES (6) are disclosed in U.S. Pat. No. 7,695,427, the disclosure of which is incorporated by reference herein and U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

B. Laparoscopic Sizing Instrument

As mentioned above, certain implants may encompass a malfunctioning LES (6) within the body to suitably assist such sphincters in properly transitioning between the occluded state and the open state. Since the diameter of the LES (6) may vary from patient to patient, it may be necessary or otherwise desirable to vary the length of an implant, to correspond with the diameter of LES (6) of the patient at hand, to thereby maximize the likelihood of a successful outcome. The suitable length of an implant (i.e. circumference of an implant when attached to the outer diameter of LES (6)) may be determined by measuring the outer diameter of the LES (6) of the patient at hand. For instance, if an implant includes an array of magnetic elements, the number of magnetic elements used for a specific implant may be determined by the outer diameter of LES (6). The larger the outer diameter, the more magnetic elements will be used; and the smaller the outer diameter, the less magnetic elements will be used.

Since the outer diameter of LES (6) may vary depending on the patient, and this may influence the configuration of an implant that is to be placed around the LES (6), it may be desirable to use a sizing instrument having an end effector that is configured to encompass and measure an outer diameter of an LES (6) of an individual patient. An operator may utilize the measurement of LES (6) to determine what size implant should be used for an individual patient. Upon identifying the appropriate size of the implant, the operator may select the appropriately sized implant from a plurality of available implants. Alternatively, the operator may modify the length of an implant to achieve the appropriate size.

Additionally, in some instances, it may be desirable to provide a sizing instrument with an auto-tensioning feature that is configured to drive the end effector of a sizing instrument into proper engagement with the outer diameter of LES (6). An auto-tensioning feature may prevent an operator from manually driving an end effector too far into engagement with the outer diameter of LES (6) such that end effector no longer suitably encompasses LES (6) for an accurate measurement of LES (6), or such that the hollow organ deforms. An auto-tensioning feature may also prevent an operator from manually driving an end effector too loose such that the end effector does not properly engage the outer diameter of LES (6). If an operator manually drives an end effector too far or too loose into engagement with the outer diameter of LES (6), this may ultimately provide an inaccurate measurement of the outer diameter of LES (6), which may lead to using an implant having an improper length. Using an implant having improper length (i.e., too long) may prevent implant of assisting LES (6) in appropriately closing. Additionally, using an implant having improper length (i.e., too short) may lead to potential dysphagia or erosion into tissue where the implant may be too tight.

An exemplary laparoscopic sizing instrument (100) having an auto-tensioning feature (166) that may be utilized to provide a proper engagement between an end effector (170) of sizing instrument (100) and the outer diameter of LES (6). Sizing instrument (100) is shown and described in U.S. patent application Ser. No. 15/908,875 entitled "Laparoscopic Sizing Instrument, filed Mar. 3, 2018, issued as U.S. Pat. No. 10,828,064 on Nov. 10, 2020, the disclosure of which is incorporated by reference herein. While sizing instrument (100) is described herein in the context of measuring the LES (6) of esophagus (2), variations of sizing instrument (100) may be used to measure the outer circumference of any other anatomical passageway, including but not limited to the pylorus, the intestinal region surrounding the ileocecal sphincter, a passageway associated with the sphincter of Oddi, a region of a urethra surrounding the urethral sphincter, a region of the rectum, a region surrounding the upper esophageal sphincter, or any other anatomical passageway.

Figure 3:
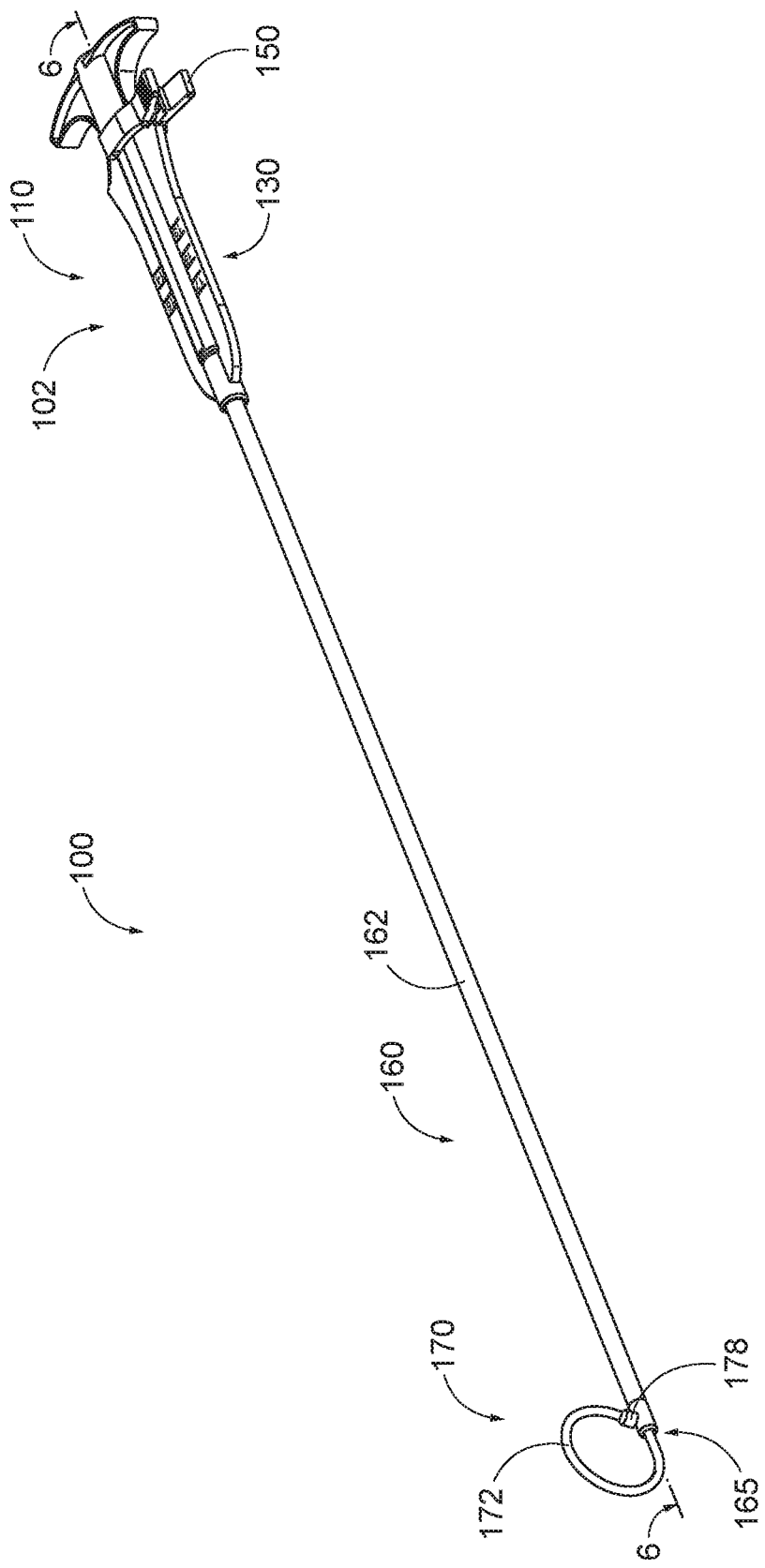
FIG. 3 depicts a perspective view of an exemplary sphincter sizing instrument that may be used to measure the biological passage of FIG. 1.
Figure 4:
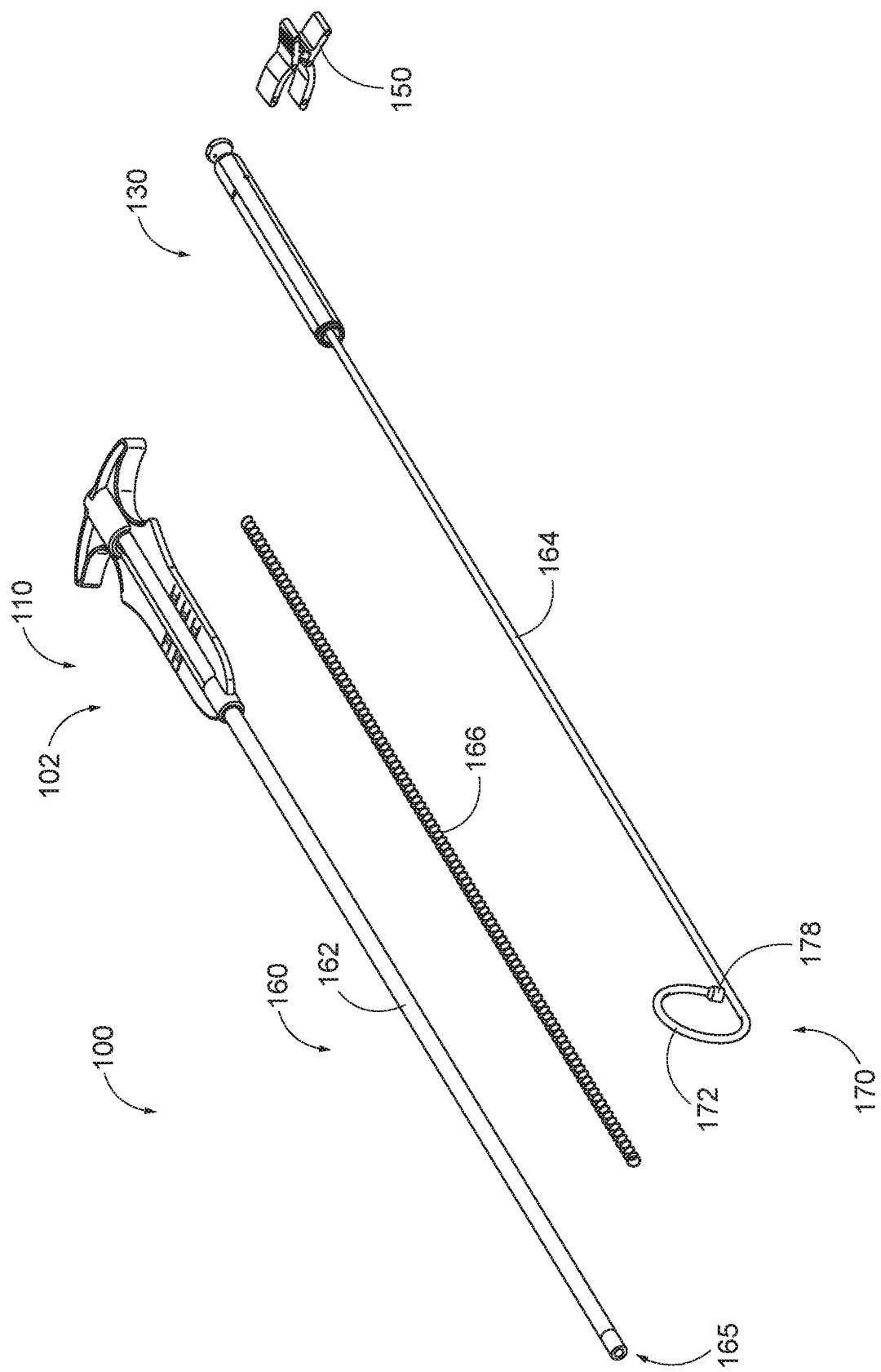
FIG. 4 depicts an exploded perspective view of the sphincter sizing instrument of FIG. 3.

As shown in FIGS. 3-4, sizing instrument (100) includes a handle assembly (102), a shaft assembly (160) extending distally from handle assembly (102), and an end effector (170) extending distally from handle assembly (102). Handle assembly (102) includes a grip portion (110), a plunger portion (130), and a locking clip (150). Shaft assembly (160) includes an exterior sheath (162), a translating interior shaft (164) slidably housed within exterior sheath (162), and auto-tensioning feature (166) housed within exterior sheath (162) and around a portion of interior shaft (164). End effector (170) includes a resilient flexible tube (172) extending distally from translating interior shaft (164), a first magnet (174) attached to a distal tip (178) of resilient flexible tube (172), and a second magnet (176) (see FIG. 6) located at an open distal end (165) of exterior sheath (162). In some variations, distal end (165) of exterior sheath (162) simply includes a ferrous cuff or other ferrous element that is configured to magnetically couple with first magnet (174), instead of including second magnet (176). Resilient flexible tube (172) defines an adjustable loop and is resiliently biased to assume the loop configuration shown in FIGS. 3-4. While sizing instrument (100) is shown to include resilient flexible tube (172), any other type of elongated resilient flexible member may be used as would be apparent to one having ordinary skill in the art in view of the teachings herein.

Figure 5A:
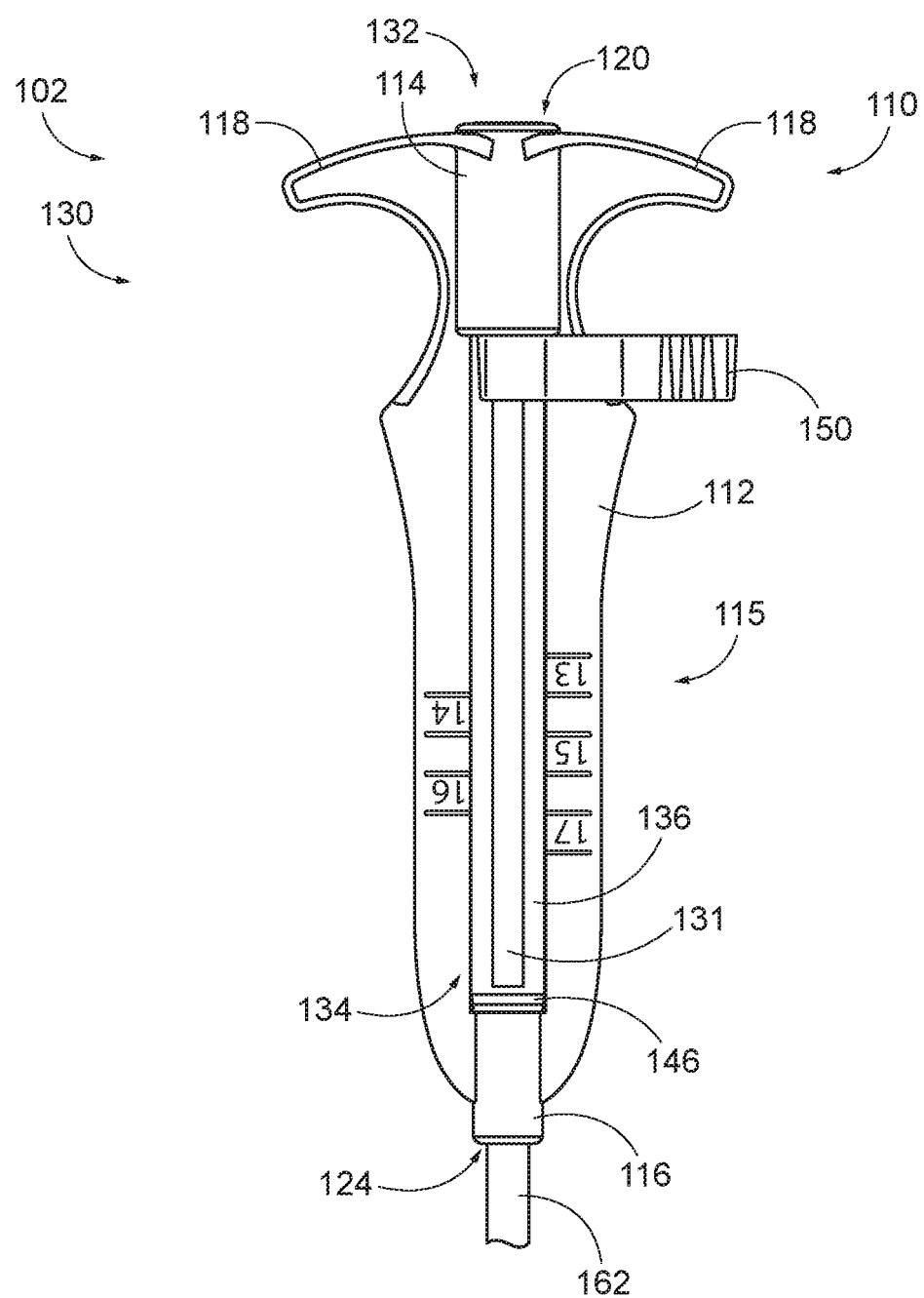
FIG. 5A depicts a top plan view of the handle assembly of the sizing instrument of FIG. 3, where a plunger portion of the sizing instrument is in a distal position corresponding with the end effector in the distal, closed, position.
Figure 5B:
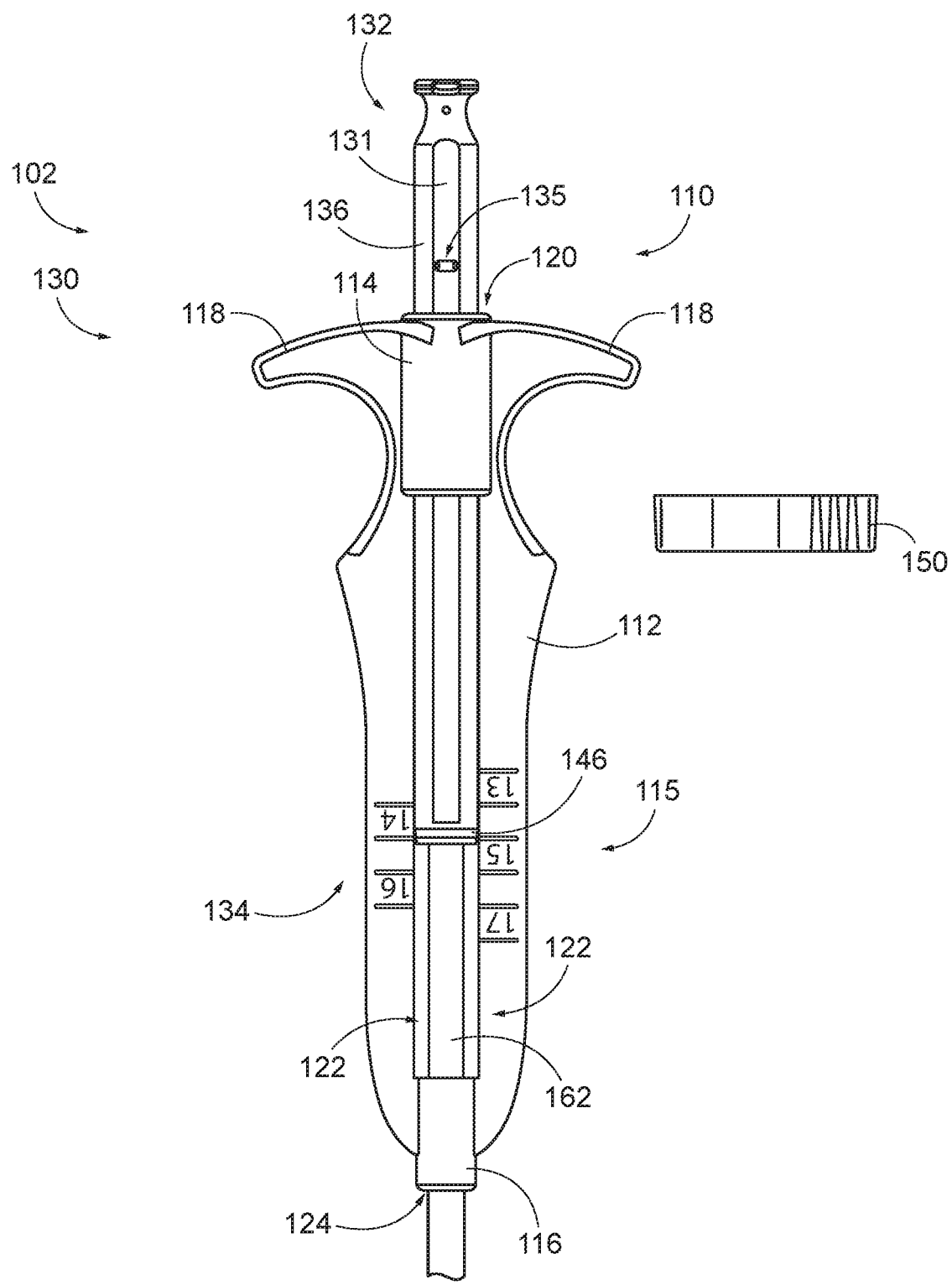
FIG. 5B depicts a top plan view of the handle assembly of FIG. 5A, where the plunger portion of FIG. 5A is in a proximal position corresponding with the end effector in the retracted, closed, position.

As shown in FIGS. 5A-5B, grip portion (110) of handle assembly (102) includes an elongated body (112) extending from a proximal sleeve (114) toward a distal locking collar (116). Grip portion (110) includes a pair of finger grips (118) extending laterally from proximal sleeve (114). Finger grips (118) may allow an operator to better grasp grip portion (110) during exemplary use. Elongated body (112) includes a plurality of indicator markings (115). As shown, indicator markings (115) have a series of sections ranging between 13 and 17, where each number corresponds with a specific sized implant. For example, if indicator (146) on plunger portion (130) is aligned within the range associated with "15" when end effector (170) sufficiently engages the outer diameter of LES (6), a corresponding size "15" implant may be used in conjunction with the recently measured LES (6). While indicator markings (115) in the current example range between 13 and 17, any suitable range may be used as would be apparent to one having ordinary skill in the art in view of the teachings herein.

Proximal sleeve (114) defines a sleeve channel (120), elongated body (112) defines a plunger window (122), and distal locking collar (116) defines a collar channel (124). Collar channel (124), plunger window (122), and sleeve channel (120) are dimensioned to receive exterior sheath (162); while distal locking collar (116) couples with exterior sheath (162) of shaft assembly (160) such that exterior sheath (162) and grip portion (110) are fixed relative to each other. Plunger window (122) and sleeve channel (120) are dimensioned to slidably receive plunger portion (130) such that plunger portion (130) may translate relative to grip portion (110). Additionally, as will be described in greater detail below, the proximal portion of exterior sheath (162) is housed within plunger window (122) and sleeve channel (120) such that exterior sheath (162) may slidably support plunger portion (130) during exemplary use.

FIGS. 5A-5B show plunger portion (130) of handle assembly (102). Plunger portion (130) extends from a proximal portion (132) to an external plunger body (134). As mentioned above, plunger portion (130) is slidably housed within sleeve channel (120) and plunger window (122) of grip portion (110). Plunger portion (130) includes an external plunger body (136) defining a cavity. External plunger body (136) includes indicator (146) and a pair of flats (131). A portion of external plunger body (136) is configured to engage a locking clip (150) while plunger portion (130) is in a distal position such that plunger portion (130) is longitudinally fixed relative to grip portion (110) while simultaneously compressing auto-tensioning feature (166). As will be described in greater detail below, locking clip (150) may be removed from plunger portion (130) such that auto-tensioning feature (166) may proximally drive plunger portion (130) relative to grip portion (110).

FIGS. 5A-5B show an exemplary use of laparoscopic sizing instrument (100). First, as shown in FIG. 5A, an operator may insert end effector (170) and a distal portion of shaft assembly (160) into a patient laparoscopically such that resilient flexible tube (172) is adjacent to LES (6). During initial insertion of end effector (170) into the patient, flexible tube (172) may be deformed to a straight configuration in order to enable flexible tube (172) to freely pass through a cannula of a trocar or some other passageway through the patient. By way of example only, plunger portion (130) and interior shaft (164) may be in a proximal-most position, with flexible tube (172) contained within exterior sheath (162), and with a proximal edge of distal tip (178) abutting a distal edge of distal end (165), while end effector (170) is being inserted into the patient. As another merely illustrative example, the operator may grasp flexible tube (172) and substantially straighten flexible tube (172) to assist in feeding flexible tube (172) through a passageway, without necessarily retracting plunger portion (130) and interior shaft (164) to a proximal-most position while inserting end effector (170) into the patient.

An operator may actuate plunger portion (130) distally relative to grip portion (110) toward the distal position (as shown in FIG. 5A), which in turn compresses auto-tensioning feature (166) between spacer tube (168) and support collar (138). The operator may hold plunger portion (130) in the distal position by overcoming the biasing force of auto-tensioning feature (166) manually or by utilizing locking clip (150). As shown, auto-tensioning feature (166) includes a compressed coil spring associated with shaft assembly (160) and is used to bias plunger portion (130) in the proximal direction relative to grip portion (110). However, auto-tensioning feature (166) may be associated with other portions of instrument (100), such as handle assembly (102); and may include any other suitable kind of biasing structure that may be used to proximally bias plunger portion (130) as would be apparent to one having ordinary skill in the art in view of the teachings herein.

Figure 6:
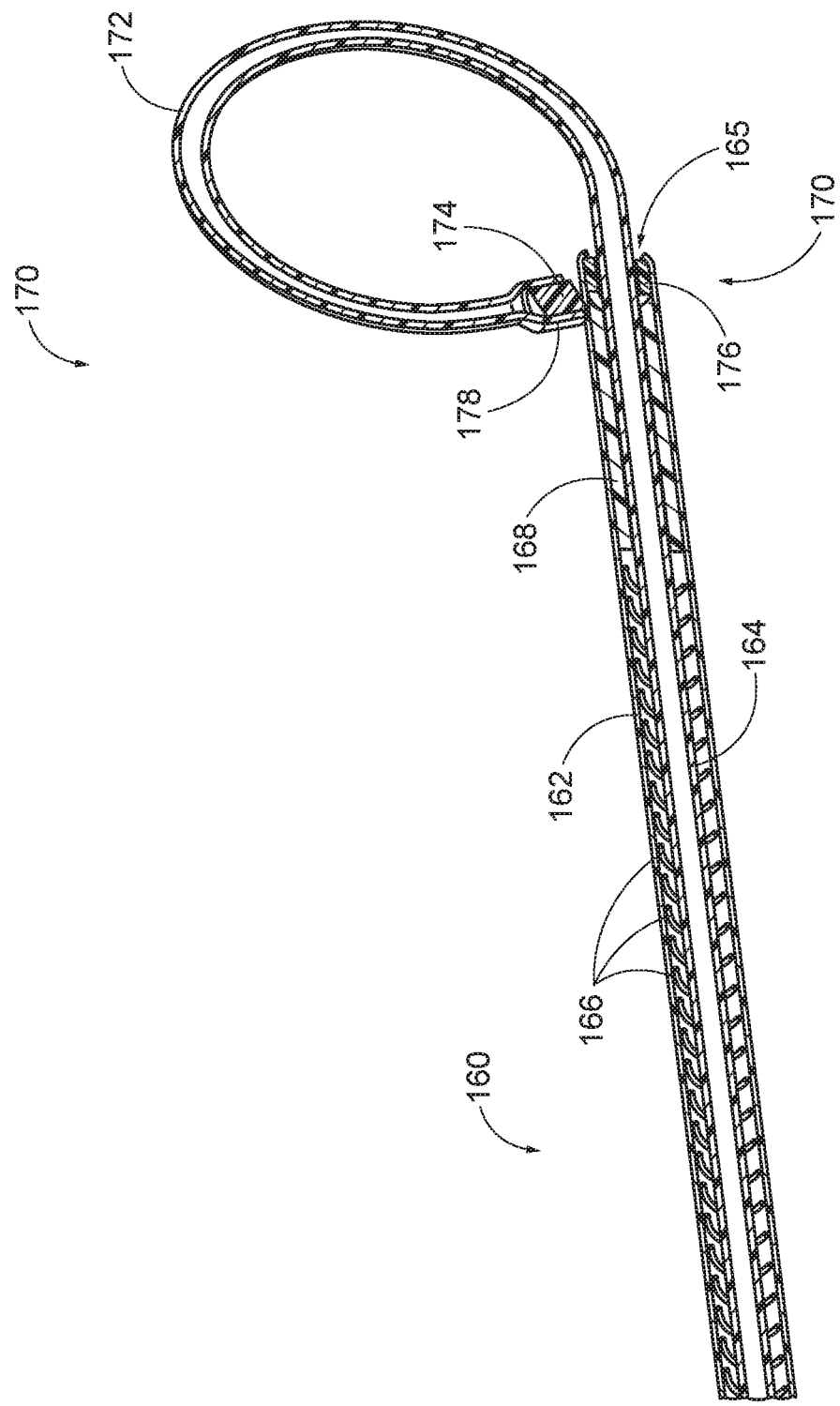
FIG. 6 depicts a cross-sectional perspective view of a shaft assembly and the end effector of the sizing instrument of FIG. 3, taken along line 6-6 of FIG. 3.

As best seen in FIG. 6, the distal portion of exterior sheath (162) houses a spacer tube (168) and second magnet (176). Spacer tube (168) and second magnet (176) are both fixed within in the interior of sheath (162). As best shown, spacer tube (168) is configured to abut against a distal end of auto-tensioning feature (166), thereby acting as a mechanical ground for auto-tensioning feature (166). As shown in FIG. 6, end effector (170) includes resilient flexible tube (172), first magnet (174) associated with distal tip (178) of resilient flexible tube (172), and second magnet (176) associated with open distal end (165) of exterior sheath (162). Resilient flexible tube (172) is biased toward a closed position. Flexible tube (172) may flex such that distal tip (178) of tube (172) does not contact with open distal end (165) of exterior sheath (162), thereby "opening" the tube (172). Resilient flexible tube (172) may include a leaf spring to bias itself toward the closed position. Alternatively, resilient flexible tube (172) may be biased to the position shown in FIG. 6 by any suitable means as would be apparent to one having ordinary skill in the art in view of the teachings herein.

Resilient flexible tube (172) is coupled to a distal end of translating interior shaft (164), which is coupled to plunger portion (130). Therefore, resilient flexible tube (172) may actuate relative to exterior sheath (162) in response to movement of plunger portion (130). Movement of resilient flexible tube (172) relative to exterior sheath (162) affects the dimension of the loop defined by resilient flexible tube (172). In particular, the loop defined by tube (172) may become larger in response to distal translation of plunger portion (130), while the loop defined by tube (172) may become smaller in response to proximal translation of plunger portion (130). Therefore, the loop defined resilient flexible tube (172) is largest when plunger portion (130) is in the most distal position. The size of the loop defined by resilient flexible tube (172) may be determined from the longitudinal position of indicator (146) on plunger portion (130) relative to indicator markings (115) on grip portion (110).

First and second magnets (174, 176) are attracted to each other such that distal tip (178) of resilient flexible tube (172) is biased toward engagement with open distal end (165) of exterior sheath (162). As noted above, second magnet (176) may be replaced with a ferrous element (e.g., metallic cuff, etc.) in some variations. In the present example, first and second magnets (175, 176) may help ensure that distal tip (178) of resilient flexible tube (172) maintains contact with open distal end (165) of exterior sheath (162) even after the loop defined by resilient flexible tube (172) decreases in diameter. In other words, first and second magnets (174, 176) may help ensure resilient flexible tube (172) remains in a closed position as the loop defined by resilient flexible tube (172) decreases in diameter due to translation of plunger portion (130). In other words, first and second magnets (174, 176) may help ensure resilient flexible tube (172) remains fully encompassed around LES (6) such that resilient flexible tube (172) may suitable engage the outer diameter of LES (6) during exemplary use.

As shown in FIG. 6, auto-tensioning feature (166) abuts against spacer tube (168) of exterior sheath (162), such that spacer tube (168) acts as a mechanical ground for auto-tensioning feature (166). Therefore, auto-tensioning feature (166) may compress and expand based on the distance defined by spacer tube (168) of exterior sheath (162) and support collar (138) of plunger portion (130). In particular, auto-tensioning feature (166) is configured to bias plunger portion (130) proximally relative to grip portion (110) of handle assembly (102). Because plunger portion (130) is slidably coupled to grip portion (110) and exterior sheath (162), the biasing force provided by auto-tensioning feature (166) may actuate plunger portion (130) and translating interior shaft (164) in the proximal direction relative to both grip portion (110) and exterior sheath (162).

II. Exemplary Alternative Sizing Instruments

Sphincter sizing instruments (200, 300, 400) provide improvements to the functionality of sphincter sizing instrument (100) to ensure that the correct size of implant is utilized in a repeatable manner. For example, to more accurately select the correct implant size, it may be beneficial to use encoded magnetic fields such that correlated magnets self-align and lock together in place. In a non-encoded magnetic field, if the magnets are off center, the operator may have to use a tool to push/realign the magnets, which may extend surgery time and/or increase the opportunity to cause trauma to the esophagus. Additionally, it would be beneficial to ensure that the first and second magnets are securely locked in place using a mechanical connection to avoid inadvertent separation of the first and second magnets which would affect the precision and accuracy of the sizing operation. It is also beneficial to ensure that a uniform compression is being applied from patient to patient and from sizing instrument to sizing instrument. Additionally, it may be desirable to alter the compression applied in a predetermined manner to have a selectable radial compression. It is also beneficial to have to utilize a sphincter sizing instrument that is readily convertible between a straight and curved configuration. These features as well as others may enable more accurate sizing of the implant using sphincter sizing instruments (200, 300, 400) as described below.

A. First Exemplary Alternative Sphincter Sizing Instrument

Figure 7:
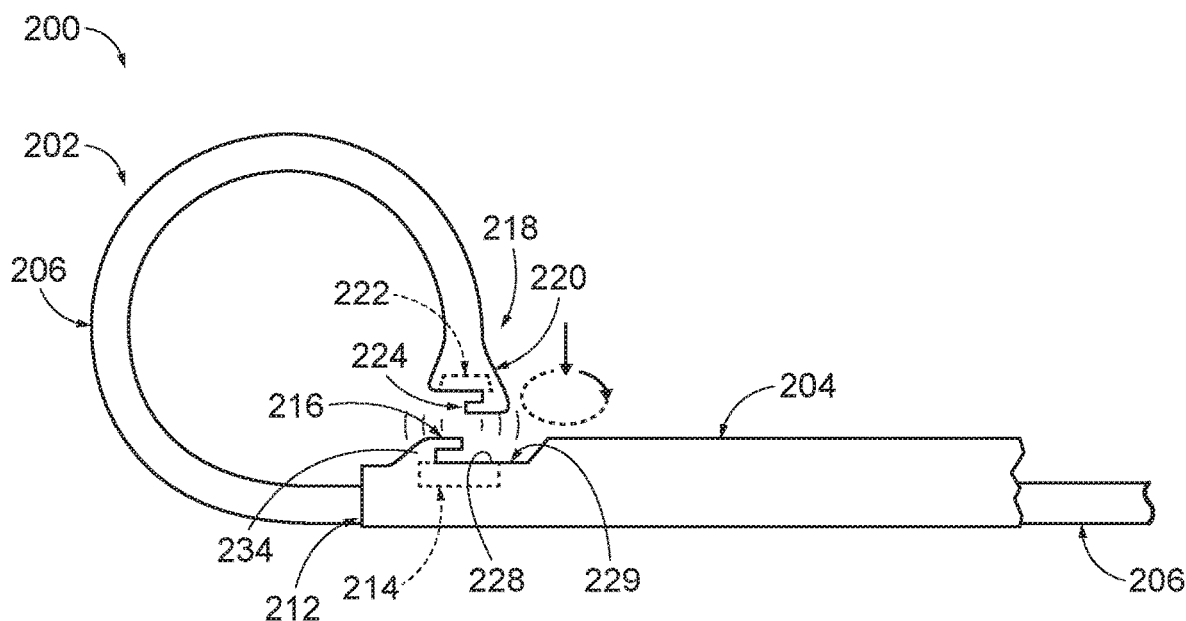
FIG. 7 depicts a top plan view of a distal portion of a first exemplary alternative sphincter sizing instrument that may be used to measure the biological passage of FIG. 1.

FIGS. 7-9D show a first exemplary alternative sphincter sizing instrument (200) that may be used to measure the biological passage of FIGS. 1-2. In other words, FIGS. 7-9D show a modified version of a distal portion (202) (shown as end effector (170) in FIGS. 4-5), such that distal portion (202) of sphincter sizing instrument (200) shown in FIGS. 7-9D may be readily incorporated into the earlier-depicted sphincter sizing instrument (100). As shown in FIG. 7, sphincter sizing instrument (200) includes a body (204), which may be similar to exterior sheath (162) shown in FIGS. 3-4, and a shaft (206) which may be similar to resilient flexible tube (172) shown in FIGS. 3-4. Body (204) defines a lumen (208) extending through body (204). Body (204) includes opposing proximal and distal ends (210, 212). Distal end (212) is similar to distal end (165) described in FIGS. 3-4 and FIG. 6, with differences described in detail below. Unlike distal end (165), distal end (212) of body (204) includes both a first magnetic coupling feature (214) and a first mechanical coupling feature (216) which are described below in greater detail with reference to FIG. 8.

Shaft (206) includes a distal end (218) and a proximal end (that may terminate into handle assembly (102) shown in FIGS. 3-5B). Distal end (218) is similar to distal tip (178) shown and described with reference to FIGS. 3-4 and FIG. 6, with differences described in detail below. Shaft (206) also includes a coupler (220) disposed at distal end (218) of shaft (206). Coupler (220) may be integrally formed as a unitary piece together with distal end (218) or may separately formed and subsequently attached using a variety of known attachment methods. Shaft (206) longitudinally translates through lumen (208) of body (204) relative to body (204). Coupler (220) includes a second magnetic coupling feature (222) and a second mechanical coupling feature (224). First magnetic coupling feature (214) is configured to oppose second magnetic coupling feature (222) of coupler (220). Second magnetic coupling feature (222) is configured to attract and subsequently couple with first magnetic coupling feature (214) to form a magnetic connection. Similarly, second mechanical coupling feature (224) is configured to couple with first mechanical coupling feature (216) to form a mechanical connection. The mechanical connection is configured to securely lock first and second mechanical coupling features (216, 224) together under a predetermined loading. This prevents premature separation of coupler (220) and distal end (212) of body (204) ensuring a more accurate and precise sizing measurement.

Figure 8:
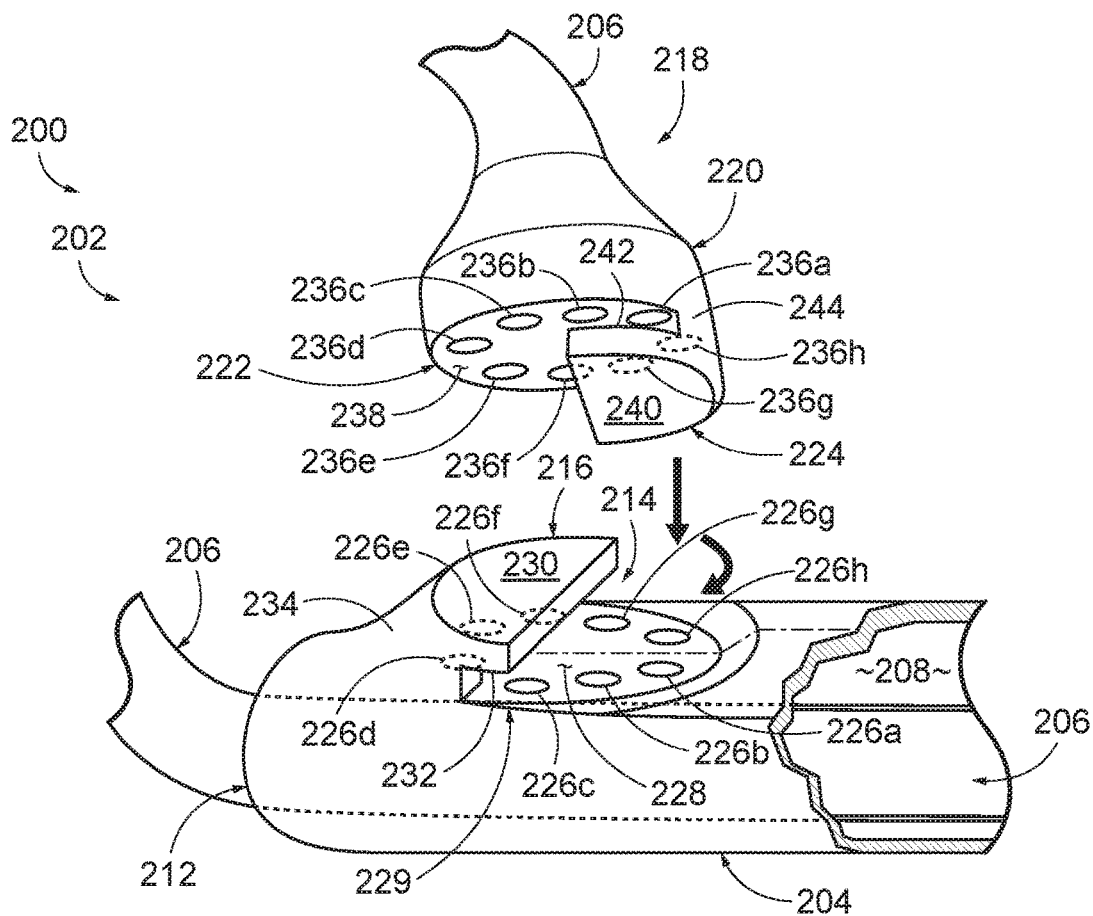
FIG. 8 depicts a distal end of the shaft being inserted and subsequently rotated to fixably couple the distal end with the coupler.

FIG. 8 shows distal end (218) of shaft (206) being actively inserted and subsequently rotated to fixably couple distal end (218) of shaft (206) with coupler (220) disposed at distal end (212) of body (204). As shown, distal end (212) of body (204) includes both a first magnetic coupling feature (214) and a first mechanical coupling feature (216). First magnetic coupling feature (214) includes an annular array of magnets (226a-h). While eight magnets (226a-h) are shown in the annular array, greater or fewer magnets are also envisioned. Magnets (226a-h) may be integrally formed as a unitary piece or comprise separately formed individual magnets. As shown, magnets (226a-h) are disposed adjacent an outer recessed surface (228) of a recessed portion (229). First mechanical coupling feature (216) includes opposing outer and inner surfaces (230, 232) that are shown as planar. Outer and inner surfaces (230, 232) extend from a neck portion (234) that tapers inward moving distally. Outer and inner surfaces (230, 232) are shown as being shaped as semicircles; however, a variety of other shapes are also envisioned.

With continued reference to FIG. 8, distal end (218) of shaft (206) includes both second magnetic coupling feature (222) and second mechanical coupling feature (224). Second magnetic coupling feature (222) includes an annular array of magnets (236a-h). While eight magnets (236a-h) are shown in the annular array, greater or fewer magnets are also envisioned. Magnets (236a-h) may be integrally formed as a unitary piece or comprise separately formed individual magnets. As shown, magnets (236a-h) are disposed adjacent an outer surface (238). First and second mechanical coupling features (216, 224) have complementary shaped features (e.g. semicircles) that collectively enable second mechanical coupling feature (224) to be locked in place with first mechanical coupling feature (216). First and second mechanical coupling features (216, 224) may be configured and operable in accordance with at least some of the teachings of U.S. Pub. No. 2011/0098731, entitled "Magnetically Assisted Clasps for Prosthetic Implants, and Related Methods," published Apr. 28, 2011, now abandoned, the disclosure of which is incorporated by reference herein. Second mechanical coupling feature (224) includes opposing outer and inner surfaces (240, 242) that are shown as planar. Outer and inner surfaces (240, 242) extend from a neck portion (244), neck portion (244) is shown being generally adjacent a proximal end in FIG. 8. Outer and inner surfaces (230, 232) are shown as being shaped as semicircles; however, a variety of other shapes are also envisioned. In the locked configuration, inner surface (232) is adjacent inner surface (242). Moreover, in the locked configuration, inner surface (232) may be directly contacting inner surface (242).

The magnetic field between first and second magnetic coupling features (214, 222) may be encoded to enable initial connection, subsequent self-aligning and subsequent locking in specified and desired orientation. For example, the magnetic connection is rotationally encoded to allow second mechanical coupling feature (224) to rotationally align with first mechanical coupling feature (216). The rotationally encoded magnetic connection creates a correlated magnetic field such that first and second mechanical coupling features (216, 224) self-align and couple together in a particular rotational orientation. The correlated magnetic field is configured to both attract coupler (220) to distal end (212) of body (204), so that first and second mechanical coupling features (216, 224) are adjacent one another in a first unlocked position. The correlated magnetic field subsequently rotates second mechanical coupling feature (224) to positively engage first mechanical coupling feature (216) in a second locked position to form the mechanical connection. Encoding the magnetic field allows for more accurate measurement than with a non-encoded magnetic field. This is because in a non-encoded magnetic field, the magnets (236a-h) may be off center indicating a size that is either smaller or larger than the actual size. Additionally, in non-encoded magnetic field, if second magnetic coupling feature (222) is noticed by the operator to be off center, the operator either has to manipulate the sizing instrument or use a tool to adjust at least one of first or second magnetic coupling feature (214, 222). This adjustment extends surgery time and/or increases the opportunity to cause trauma to the esophagus.

First magnetic coupling feature (214) includes magnets (226a-h), where magnets (226a, 226c, 226e, 226h) have a first polarity and magnets (226b, 226d, 226f, 226h) have a second polarity that is opposite the first polarity. Similarly, second magnetic coupling feature (222) includes magnets (236a-h). Magnets (236a, 236c, 236e, 236h) have the second polarity, while magnets (226b, 226d, 226f, 226h) have the first polarity. Alignment of first and second magnetic coupling features (214, 222) causes magnet (226a) to couple together with magnet (236a), magnet (226b) to couple together with magnet (236b), magnet (226c) to couple together with magnet (236c), magnet (226d) to couple together with magnet (236d), magnet (226e) to couple together with magnet (236e), magnet (226f) to couple together with magnet (236f), magnet (226g) to couple together with magnet (236g), and magnet (226h) to couple together with magnet (236h). Alignment of first and second magnetic coupling features (214, 222) causes magnet (226a) to repel magnets (236b, 236h), magnet (226b) to repel magnets (236a, 236c), magnet (226c) to repel magnets (236b, 236d), magnet (226d) to repel magnets (236c, 236e), magnet (226e) to repel magnets (236d, 2360, magnet (226f) to repel magnets (236e, 236g), magnet (226g) to repel magnets (236f, 236h), and magnet (226h) to repel magnets (236a, 236g).

Similar to sizing instrument (100) previously described with respect to FIGS. 3-4, sphincter sizing instrument (200) may include a handle assembly similar to handle assembly (102), a shaft assembly similar to shaft assembly (104), and an end effector similar to end effector (170). Handle assembly includes a handle body similar to handle body and a plunger portion similar to plunger portion (130) that is slidably coupled with handle body. Shaft assembly extends distally from handle assembly. Shaft assembly includes an external sheath fixed to the handle body, and an interior shaft similar to interior shaft (164) coupled to the plunger portion. Interior shaft is slidable relative to the external sheath. End effector configured to encompass a bodily lumen. End effector includes a flexible member similar to resilient flexible tube (172), a first mechanical coupling feature (216) fixed to distal tip of flexible member, a first magnetic coupling feature (214) fixed to distal tip of flexible member, second magnetic coupling feature (222) fixed to external sheath, and second mechanical coupling feature (224) fixed to external sheath. Flexible member extends distally from interior shaft. First and second magnetic coupling features (214, 222) are configured to be magnetically attracted to each other to define an adjustable loop. First and second mechanical coupling features (216, 224) are configured to selectively lock with each other. Sphincter sizing instrument (200) may also include an auto-tensioning feature similar to auto-tensioning feature (166) that is configured to bias plunger portion proximally relative to handle body.

Figure 9A:
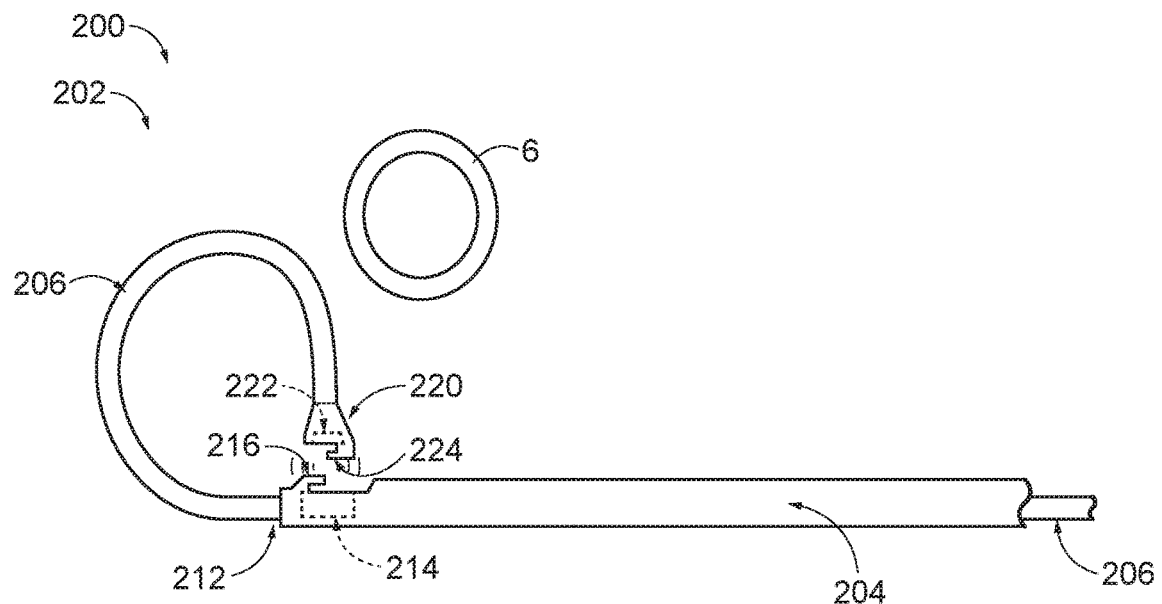
FIG. 9A depicts a top plan view of the body and the shaft of FIG. 7 placed adjacent to a lower esophageal sphincter.

FIGS. 9A-9D show an exemplary method of using sphincter sizing instrument (200). FIG. 9A shows a top plan view of body (204) and shaft (206) of FIG. 7 placed adjacent to LES (6). As shown in FIG. 9A, after distal end (218) of shaft (206) has been inserted into the patient, distal end (218) of shaft (206) is positioned near the LES (6). As shown, distal end (218) of shaft (206) extends distally from distal end (212) of body (204).

Figure 9B:
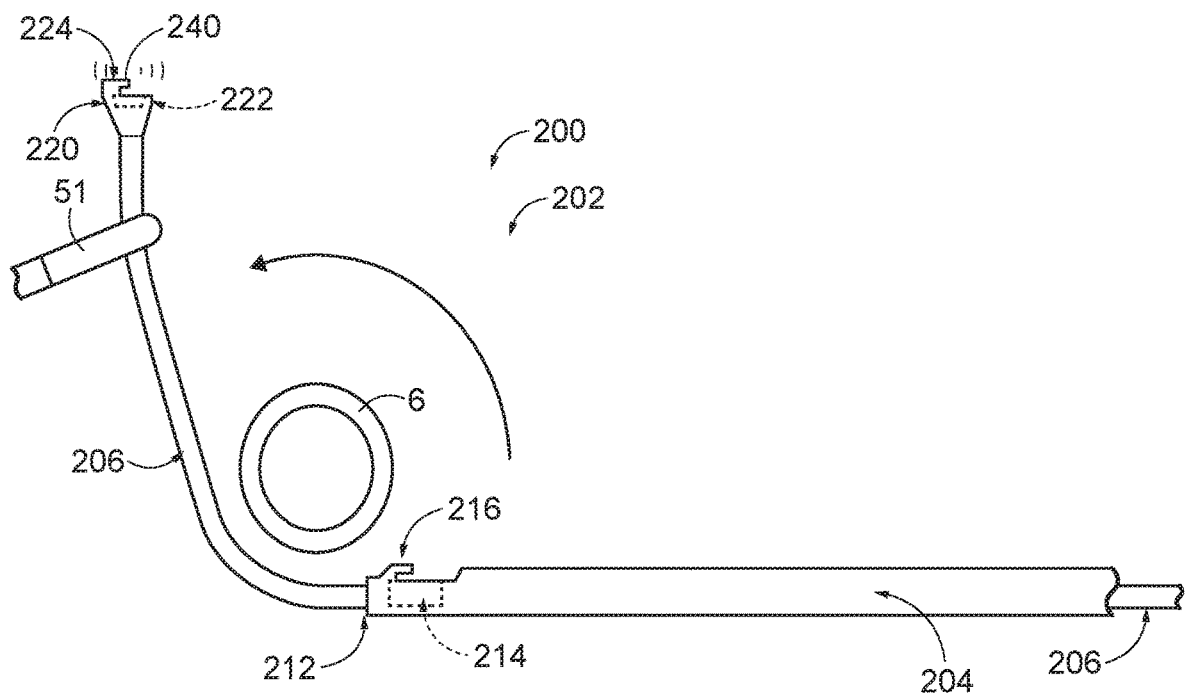
FIG. 9B depicts a top plan view of the body and the shaft of FIG. 9A, but with the shaft being placed at least partially around the lower esophageal sphincter in an open configuration.

FIG. 9B shows a top plan view of shaft (206) and body (204) of FIG. 9A, but with the shaft being placed at least partially around LES (6) in an open configuration. The operator may grasp and pull a portion of shaft (206) in order to overcome the biasing force of first and second magnetic coupling features (214, 222) to transition shaft (206) from the closed position to the opened position. As shown, the operator may use a conventional grasping instrument (51) to pull shaft (206) into the opened position. Alternatively, any other suitable instrument may be used as would be apparent to one having ordinary skill in the art in view of the teachings herein. With distal end (218) of shaft (206) in the opened position, the operator may adjust the position of coupler (220) such that LES (6) is surrounded by shaft (206) as coupler (220) approaches distal end (212) of body (204).

Figure 9C:
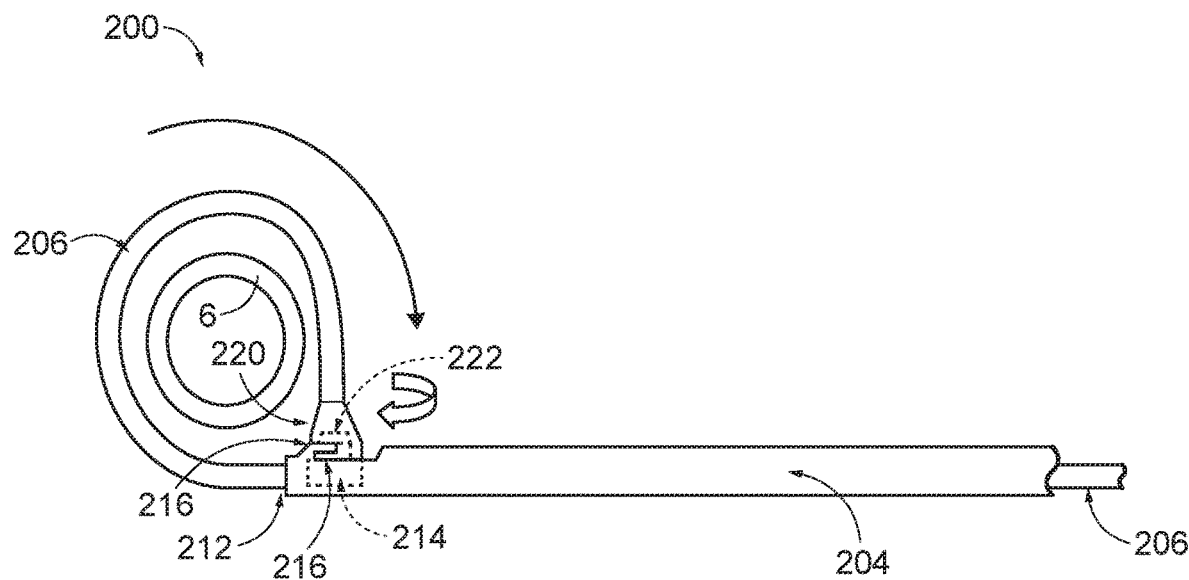
FIG. 9C depicts a top plan view of the body and the shaft of FIG. 7, but with the shaft being placed at completely around the lower esophageal sphincter in a closed loose configuration.

FIG. 9C shows a top plan view of shaft (206) and body (204) of FIG. 9B, but with shaft (206) being placed completely around LES (6) in a closed loose configuration. As shown, the operator may release shaft (206) from grasping instrument (51), such that shaft (206) resiliently returns to the closed configuration. At this point, LES (6) is fully circumferentially encompassed by shaft (206). However, shaft (206) is not engaged with LES (6) to suitably measure the outer diameter of LES (6) as there is slack around LES (6).

Figure 9D:
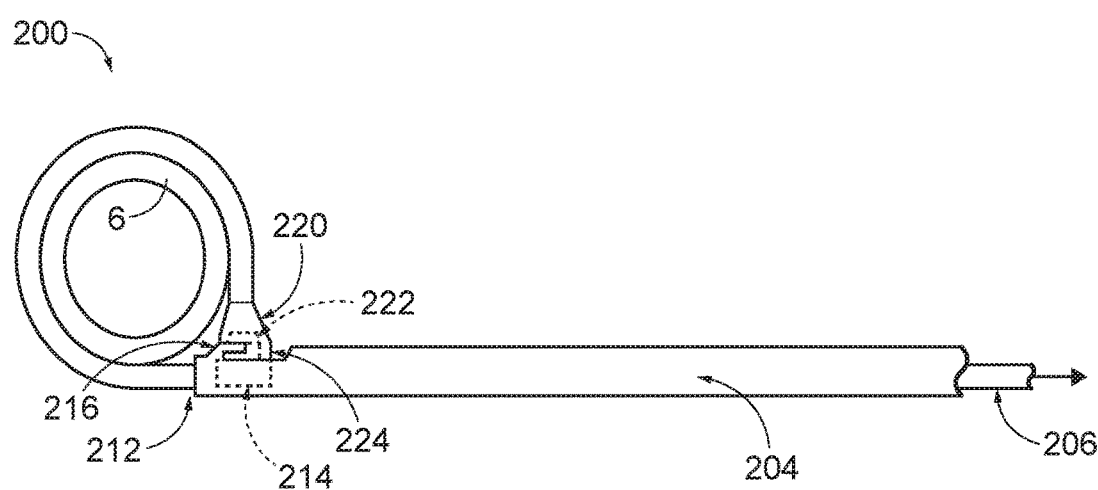
FIG. 9D depicts a top plan view of the body and the shaft of FIG. 7, but with the shaft being placed completely around the lower esophageal sphincter in a closed snug configuration.

FIG. 9D shows a top plan view of body (204) and shaft (206) of FIG. 9C, but with shaft (206) placed completely around LES (6) in a closed configuration, where shaft (206) is snug with LES (6). Shaft (206) does not inwardly bias (i.e. squeeze) LES (6). As previously described, an auto-tensioning feature similar to auto-tensioning feature (166) may be configured to decrease the diameter of the adjustable loop defined by shaft (206) until shaft (206) sufficiently engages the outer diameter of LES (6) (as shown in FIG. 9D). With shaft (206) suitably engaging LES (6), a portion of shaft (206) is withdrawn proximally. At this point, the operator may visually confirm the location of an indicator, similar to indicator (146), relative to indicator markings to determine the proper implant size. Now having suitably measured LES (6), the operator may remove sphincter sizing instrument (200) from the patient through any suitable technique that would be apparent to one having ordinary skill in view of the teachings herein. For example, the operator may use conventional grasping instrument (51) to remove sphincter sizing instrument (200). The operator may utilize the measurement of LES (6) to select an implant that is most appropriate for the patient at hand, to modify an implant so that the implant is at the most appropriate configuration for the patient at hand, and/or for any other purposes.

B. Second Exemplary Alternative Sphincter Sizing Instrument

FIGS. 10A-11C show a second exemplary alternative sphincter sizing instrument (300) that may be used to measure the biological passage of FIGS. 1-2. In other words, FIGS. 7-9D show a modified version of a distal portion (302) (shown as end effector (170) in FIGS. 4-5), such that distal portion (302) of sphincter sizing instrument (300) shown in FIGS. 7-9D may be readily incorporated into the earlier-depicted sphincter sizing instrument (100). As shown, sphincter sizing instrument (300) includes a body (304), which may be similar to exterior sheath (162) shown in FIGS. 3-4, and a shaft (306) which may be similar to resilient flexible tube (172) shown in FIGS. 3-4.

Body (304) defines a lumen (308) extending through body (304). Body (304) includes opposing proximal and distal ends (310, 212). As shown, distal end (312) may be shaped as an annular ring that has a greater diameter than the rest of body (304). Distal end (312) is similar to distal end (165) described in FIGS. 3-4 and FIG. 6, with differences described in detail below. Unlike distal end (212) that includes a first mechanical coupling feature (216), distal end (312) is not shown to include a mechanical coupling feature.

Shaft (306) includes a distal end (318) and a proximal end (that may terminate into handle assembly (102) shown in FIGS. 3-5B). Distal end (318) is similar to distal tip (178) shown and described with reference to FIGS. 3-4 and FIG. 6, with differences described in detail below. Additionally, unlike distal end (218) that includes second mechanical coupling feature (224), distal end (318) is not shown to include a mechanical coupling feature. Shaft (306) includes a coupler (320) disposed at distal end (318) of shaft (306). Coupler (320) may be integrally formed as a unitary piece together with distal end (318) or may be separately formed and subsequently attached using a variety of known attachment methods. Shaft (306) longitudinally translates through lumen (308) relative to body (304). Coupler (320) includes a second magnetic coupling feature (322). First magnetic coupling feature (314) is configured to oppose second magnetic coupling feature (322) of coupler (320). Second magnetic coupling feature (322) is configured to attract and subsequently couple with first magnetic coupling feature (314) to form a magnetic connection. The magnetic connection is configured to provide a predetermined radial compression during sizing measurement to define a resting sphincter state.

Figure 10A:
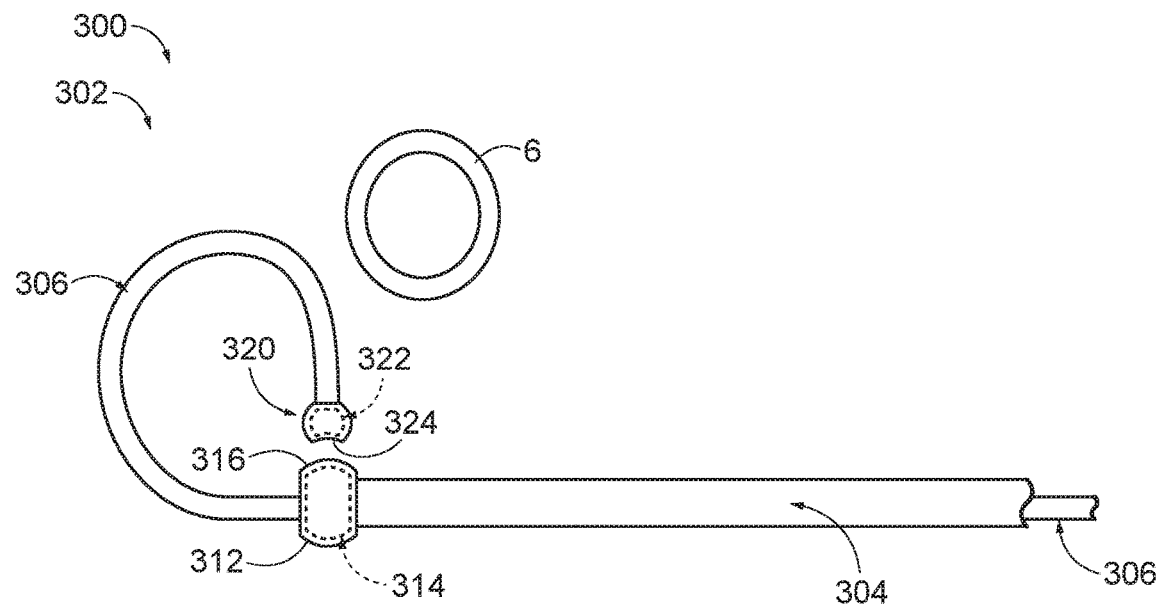
FIG. 10A depicts a top plan view of a second exemplary alternative sphincter sizing instrument that may be used to measure the biological passage of FIG. 1; where the sizing instrument includes a body and a shaft that are placed adjacent to the lower esophageal sphincter.
Figure 10B:
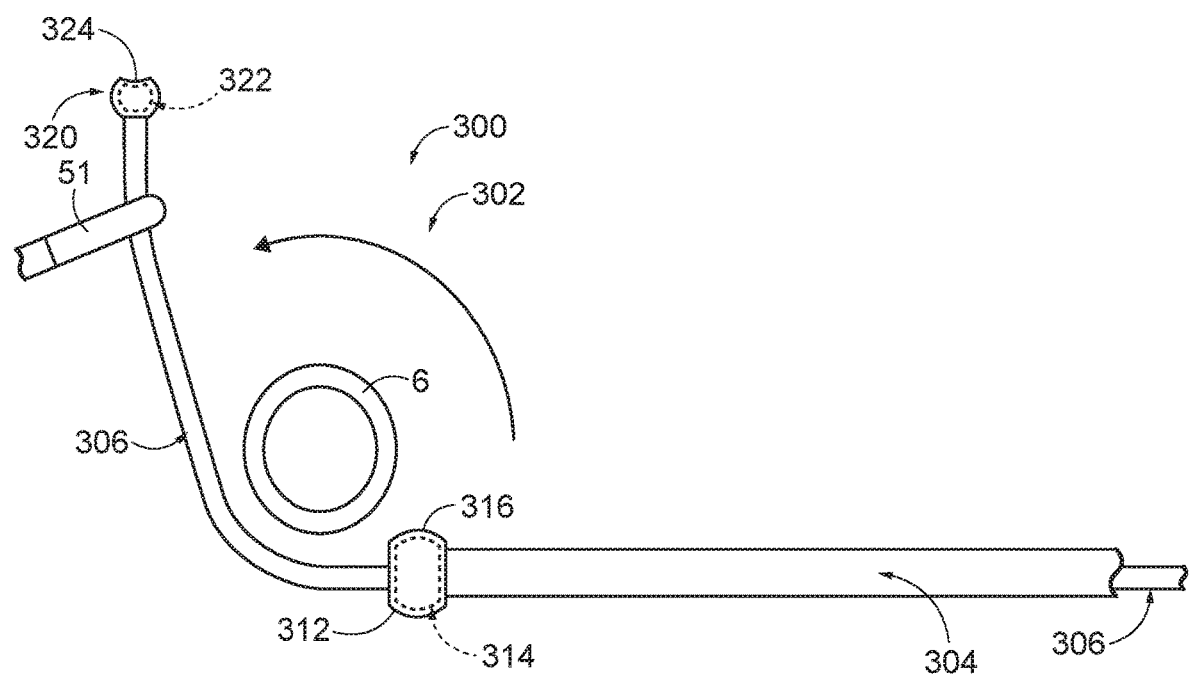
FIG. 10B depicts a top plan view of the body and the shaft of FIG. 10A, but with the shaft being placed at least partially around the lower esophageal sphincter in an open configuration.
Figure 10C:
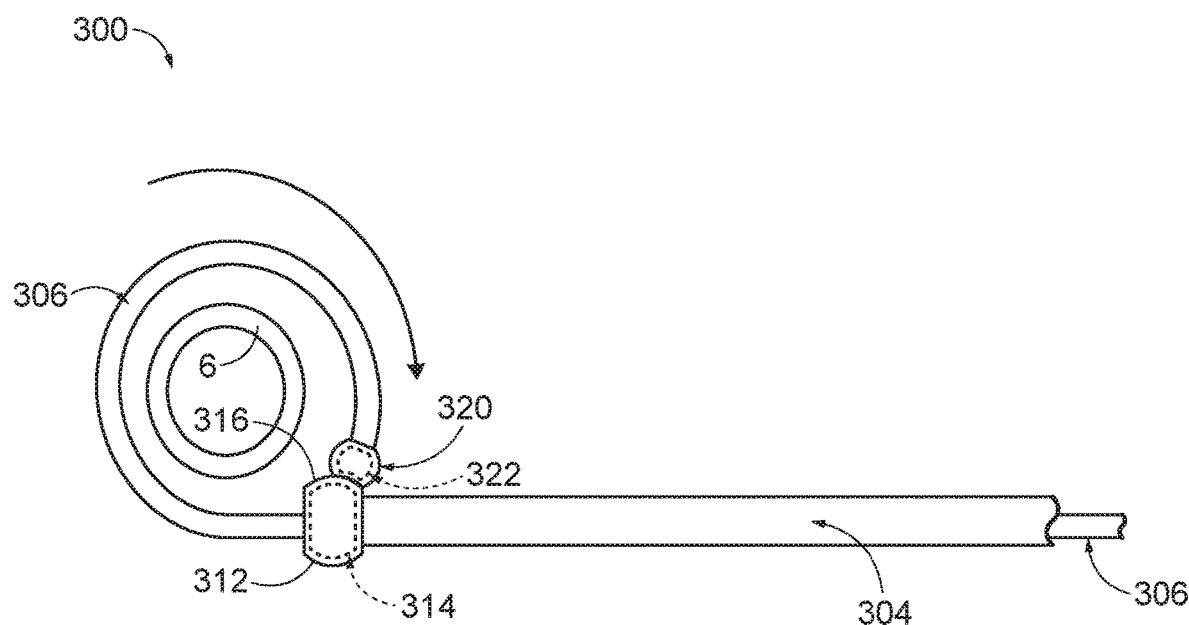
FIG. 10C depicts a top plan view of the body and the shaft of FIG. 10B, but with the shaft placed completely around the lower esophageal sphincter in a closed loose configuration.
Figure 10D:
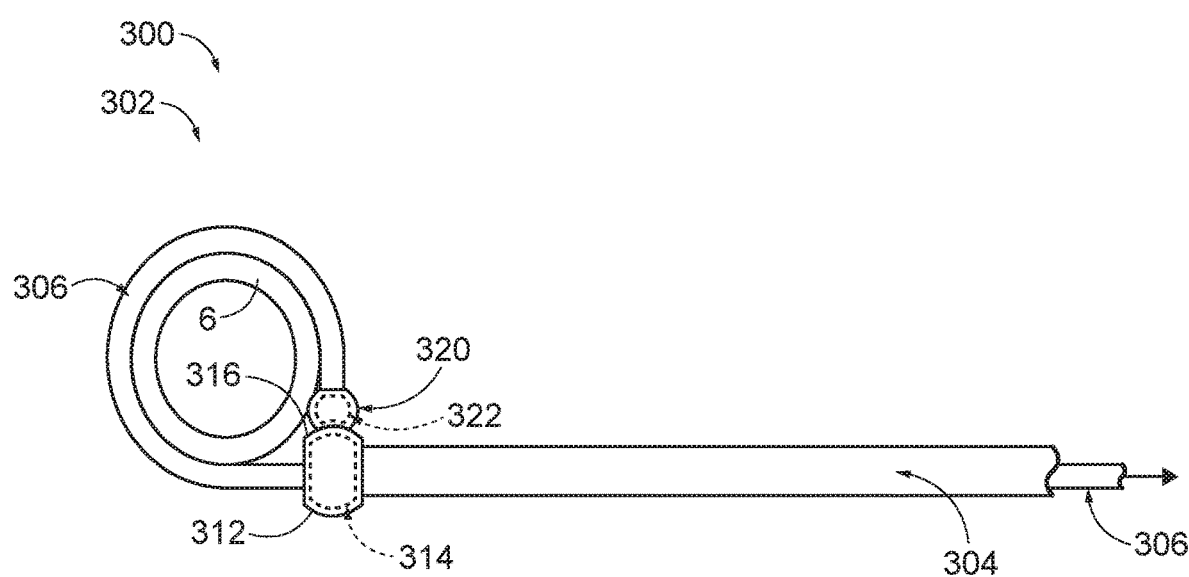
FIG. 10D depicts a top plan view of the body and the shaft of FIG. 10C, but with the shaft placed completely around the lower esophageal sphincter in a closed snug configuration.

FIGS. 10A-10D show an exemplary method of using sphincter sizing instrument (300). The method described for sphincter sizing instrument (300) is similar to the method described with respect to sphincter sizing instrument (300) in FIGS. 9A-9D. FIG. 10A shows a top plan view of sphincter sizing instrument (300) that may be used to measure the biological passage of FIG. 1. FIG. 10B shows a top plan view of shaft (306) and body (304) of FIG. 10A, but with shaft (306) being placed at least partially around LES (6) in an open configuration. FIG. 10C shows a top plan view of shaft (306) and body (304) of FIG. 10B, but with shaft (306) being placed completely around LES (6) in a closed but loose configuration. FIG. 10D shows a top plan view of body (304) and shaft (306) of FIG. 10C, but with shaft (306) being placed completely around LES (6) in a closed and snug configuration. In the closed and snug configuration, no space exists between shaft (306) and LES (6), but shaft (306) does not inwardly bias (i.e. squeeze) LES (6). As shown in FIG. 10D, proximal end of shaft (306) is configured to be moved relative to distal end (312) of body (304) to reduce an area of a loop defined by shaft, where predetermined pull-off force is same through a range of sizes of loop which enable first and second magnetic coupling features (314, 322) to form magnetic connection at a range of different angles.

Figure 11A:
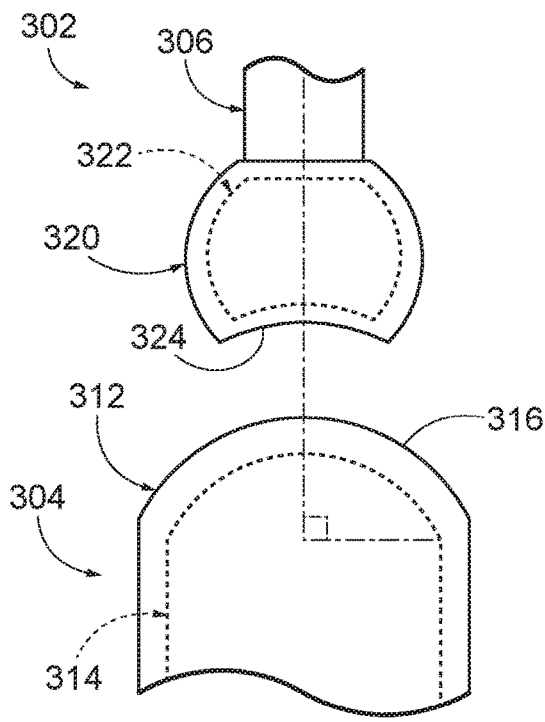
FIG. 11A depicts a coupler attracted to a distal end of the body of FIG. 10A, for a medium-sized lower esophageal sphincter.
Figure 11B:
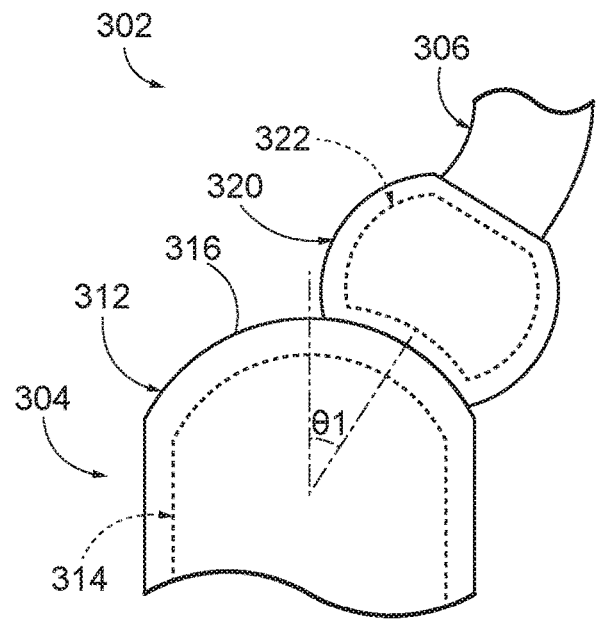
FIG. 11B depicts the coupler coupled with the distal end of the body of FIG. 11A, but for a large-sized lower esophageal sphincter.
Figure 11C:
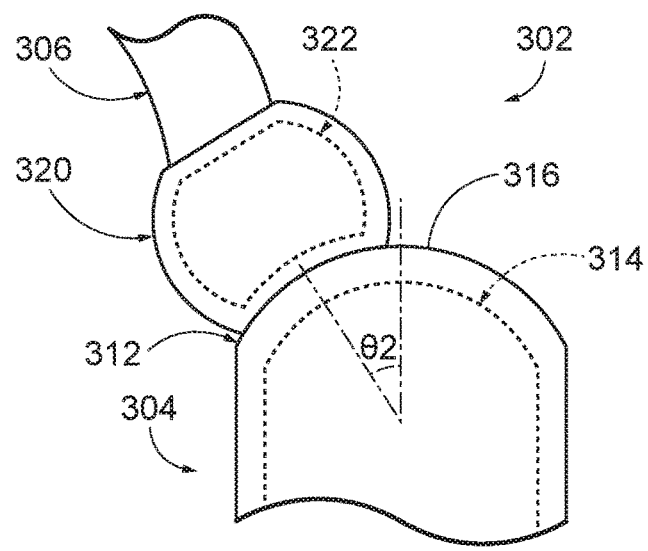
FIG. 11C depicts the coupler coupled with the distal end of the body of FIG. 11A, but for a small-sized lower esophageal sphincter.

As shown in FIGS. 10A-10D, and in greater detail in FIGS. 11A-11C, first magnetic coupling feature (314) has a convex interface surface (324), and second magnetic coupling feature (322) has concave interface surface (326). However, it is also envisioned that this relationship may be reversed such that first magnetic coupling feature (314) has a concave interface surface and second magnetic coupling feature (322) has a convex interface surface. As a result, coupler (320) is configured to align at a range of different angles relative to distal end (312) of body (304). In other words, given the complementary shapes of first and second magnetic coupling features (314, 322), the suitable radius of engagement between first and second magnetic coupling features (314, 322) is increased. It is envisioned that convex interface surface (324) of first magnetic coupling feature (314) may slide relative to concave interface surface (326) of second magnetic coupling feature (322), such that first and second magnetic coupling features (314, 322) maintain constant contact over an increased range of angles.

FIGS. 11A-11C show how sphincter sizing instrument (300) is configured to accurately measure LES (6) having different sizes. Sphincter sizing instrument (300) is configured to provide a compressive force during measurement in order to define the resting sphincter state. FIG. 11A shows coupler (320) attracted to distal end (312) of body (304) of FIG. 10A, for a medium-sized LES (6). For example, coupler (320) couples with distal end (312) head on. Alternatively, FIG. 11B shows coupler (320) attracted to distal end (312) of body (304) for a large-sized LES (6). For example, coupler (320) couples with distal end (312) at a first angle theta (01). FIG. 11C shows coupler (320) attracted to distal end (312) of body (304) for a small-sized LES (6). For example, coupler (320) couples with distal end (312) at a second angle theta (02).

The magnetic connection between first and second magnetic coupling features (314, 322) have a predetermined pull-off force. The predetermined pull-off force is defined as the minimal mechanical separation force that exceeds the magnetic attractive force. The pull-off force is configured to break magnetic connection between first or second magnetic coupling features (314, 322). Predetermined radial compression is selectable by a user using a selection tool (e.g. a chart, table, or computer program), where the selection tool includes a predetermined range of acceptable predetermined radial compression values. Selections outside of predetermined range of acceptable predetermined radial compression values are configured to be produce a warning, error, or may be even prevented.

The ability to create a known or selectable pull-off force allows the operator to define a repeatable compression from sizing instrument to sizing instrument. Selectable radial compression during the sizing operation aids to define implant compression. Selectable radial compression may be accomplished using convex interface surface (324) of distal end (312) of body (304) and concave interface surface (326) of coupler (320). These convex and concave interface surfaces (324, 326) allow second magnetic coupling feature (322) to seat normally with first magnetic coupling feature (314) over a wide range of LES (6) sizes.

As shown, first magnetic coupling feature (314) may alternatively have a flat faced interface surface instead of a concave interface surface (326). In this manner, convex and concave interface surfaces (324, 326) have the same contact interface regardless of the particular angle. Additionally, the intensity of first or second magnetic coupling features (314, 322) may be changed as desired. In some variations, distal end (312) of body (304) simply includes a ferrous cuff or other ferrous element that is configured to magnetically couple with second magnetic coupling feature (322) of coupler (320). Alternatively, distal end (318) of shaft (306) simply includes a ferrous cuff or other ferrous element that is configured to magnetically couple with first magnetic coupling feature (314). For example, a weaker magnet may be composed from a different material composition than a stronger magnet. Alternatively or in addition to a different material composition, a coating may be applied to the magnet. For example, altering the coating may include increasing the thickness of the coating which in turn increases the distance the magnet is separated from the metallic collar which effectively reduces the pull-off force.

C. Third Exemplary Alternative Sphincter Sizing Instrument

Figure 12:
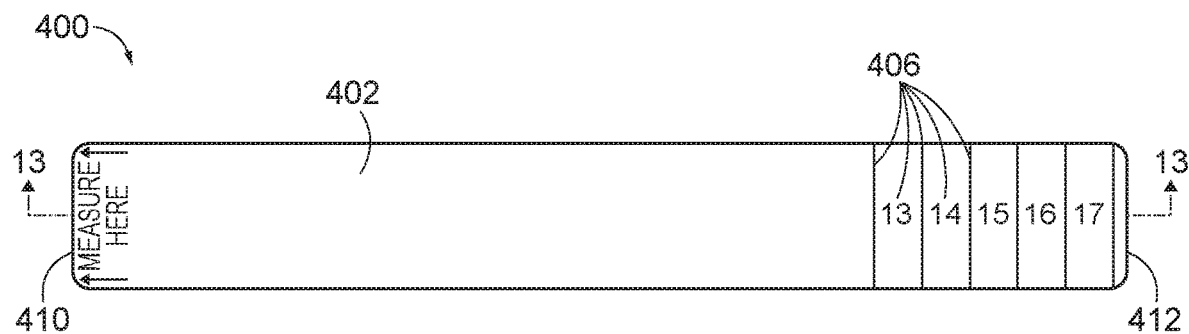
FIG. 12 depicts a side plan view of a third exemplary alternative sphincter sizing instrument that may be used to measure the biological passage of FIG. 1, where the sizing instrument is in a straight configuration.
Figure 13:
FIG. 13 depicts a sectional view of the sphincter sizing instrument of FIG. 12, taken along line 13-13 of FIG. 12.
Figure 14:
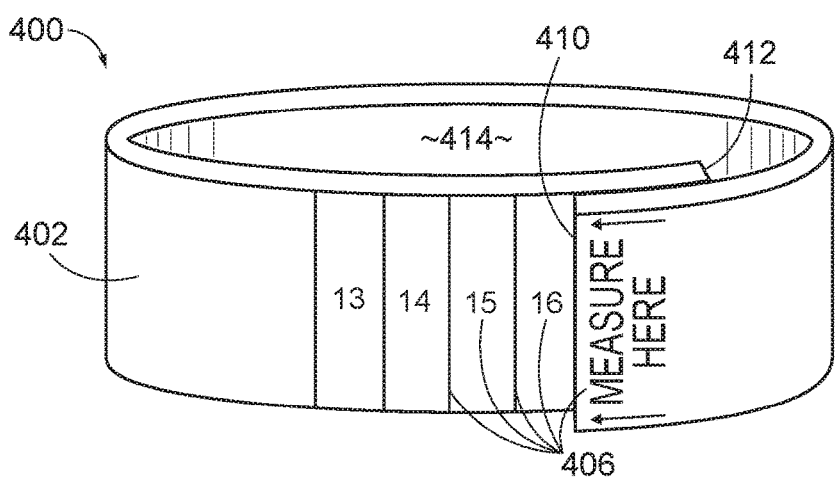
FIG. 14 depicts the sizing instrument of FIG. 12 in a curved configuration.

FIGS. 12-14 show a third exemplary alternative sphincter sizing instrument (400) that may be used to measure the biological passage of FIG. 1. Sphincter sizing instrument (400) includes a biocompatible cover (402) and a body (404)

(see FIG. 13). FIG. 12 shows a side plan view of sphincter sizing instrument (400) in an open undeployed configuration (e.g. straight configuration). As shown in FIG. 12, cover (402) includes indicator markings (406) configured to indicate the size of esophagus to select the correct implant size. The indicator markings (406) are located at specific locations correlating to sizes between first and second terminal ends (410, 412). Indicator markings (406) may be similar to indicator markings (115). Cover (402) may be formed from a fabric, silicone, plastic, or any other suitable material or combination of materials. Sphincter sizing instrument (400) may be in the straight configuration during insertion (see FIG. 12), and subsequently form a curved configuration when wrapped around LES (6) when pressure is applied (see FIG. 14).

FIG. 13 shows a sectional view of sphincter sizing instrument (400) of FIG. 12, taken along line 13-13 of FIG. 12. Body (404) includes a plurality of layered flexible bistable spring bands (408) that are disposed within cover (402). According to an exemplary embodiment, sphincter sizing instrument (400) is similar to a "slap bracelet" or "snap bracelet". As shown, layered flexible stainless steel bistable spring bands (408) are sealed within cover (402). Body (404) has a bistable bias between the straight configuration and the curved configuration.

FIG. 14 shows that when sphincter sizing instrument (400) is in the curved configuration, where layered flexible bistable spring bands (408) have a predetermined radial compression value. In the curved configuration, sphincter sizing instrument (400) defines a lumen (414). Creating a biasing aspect to the sizing loop of sphincter sizing instrument (400) provides a known threshold of loop inner compression while an operator holds the end of the loop. For example, similar to FIGS. 9B and 10B, the operator may hold the end of the loop using conventional grasping instrument (51) shown in FIGS. 9B and 10B.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A sphincter sizing instrument comprising: (a) a body that defines a lumen, wherein the body includes opposing proximal and distal ends, wherein the distal end includes: (1) a first magnetic coupling feature, and (2) a first mechanical coupling feature; (b) a shaft that longitudinally translates through the lumen relative to the body, wherein the shaft includes: (1) opposing proximal and distal ends, and (2) a coupler coupled with the distal end, wherein the coupler includes: (A) a second magnetic coupling feature configured to attract and couple with the first magnetic coupling feature to form a magnetic connection, and (B) a second mechanical coupling feature configured to couple with the first mechanical coupling feature to form a mechanical connection.

Example 2

The sphincter sizing instrument of Example 1, wherein the first magnetic coupling feature is configured to oppose the second magnetic coupling feature of the coupler.

Example 3

The sphincter sizing instrument of any one or more of Examples 1 through 2, wherein the mechanical connection is configured to secure the first and second mechanical coupling features together under a predetermined loading.

Example 4

The sphincter sizing instrument of any one or more of Examples 1 through 3, wherein the magnetic connection is rotationally encoded to allow the second mechanical coupling feature to rotationally align with the first mechanical coupling feature to form the mechanical connection.

Example 5

The sphincter sizing instrument of any one or more of Examples 1 through 4, wherein the magnetic connection is rotationally encoded to create a correlated magnetic field such that the first and second mechanical coupling features self-align and couple together in a particular rotational orientation.

Example 6

The sphincter sizing instrument of Example 5, wherein the correlated magnetic field is configured to both attract the coupler to the distal end of the body such that the first and second mechanical coupling features are adjacent one another in a first unlocked position and subsequently rotate the second mechanical coupling feature to positively engage the first mechanical coupling feature in a second locked position.

Example 7

The sphincter sizing instrument of any one or more of Examples 1 through 6, wherein the first magnetic coupling feature includes at least first and second spaced magnets, wherein the first magnet has a first polarity and the second magnet has a second polarity, wherein the second magnetic coupling feature includes at least third and fourth spaced magnets, wherein the third magnet has the second polarity and the fourth magnet has the first polarity, wherein alignment of the first and second magnetic coupling features causes the first and third magnets to couple together and the second and fourth magnets to couple together.

Example 8

The sphincter sizing instrument of Example 7, wherein alignment of the first and second magnetic coupling features causes the first and fourth magnets to repel one another, and the second and third magnets to repel one another.

Example 9

The sphincter sizing instrument of any one or more of Examples 1 through 6, wherein the first magnetic coupling feature includes at least first, second, and third spaced magnets, wherein the first magnet has a first polarity, the second magnet has a second polarity, and the third magnet has the first polarity, wherein the second magnetic coupling feature includes at least fourth, fifth, and sixth spaced magnets, wherein the fourth magnet has the second polarity, the fifth magnet has the first polarity, and the sixth magnet has the second polarity, wherein alignment of the first and second magnetic coupling features causes the first and fourth magnets to couple together, the second and fifth magnets to couple together, and the third and sixth magnets to couple together.

Example 10

The sphincter sizing instrument of any one or more of Examples 1 through 2 or 5 through 9, wherein the first or second magnetic coupling feature is concave, wherein the other of the first or second magnetic coupling feature is convex, such that the coupler configured to align at a range of different angles relative to the distal end of the body.

Example 11

The sphincter sizing instrument of any one or more of Examples 1 through 10, wherein the magnetic connection is configured to provide a predetermined radial compression during sizing measurement to define a resting sphincter state.

Example 12

The sphincter sizing instrument of Example 11, wherein the predetermined radial compression is selectable by a user using a selection tool, wherein the selection tool includes a predetermined range of acceptable predetermined radial compression values.

Example 13

The sphincter sizing instrument of any one or more of Examples 1 through 12, wherein the proximal end of the shaft is configured to be moved relative to the distal end of the body to reduce an area of a loop defined by the shaft.

Example 14

The sphincter sizing instrument of any one or more of Examples 1 through 13, wherein the magnetic connection between the first and second magnetic coupling features have a predetermined pull-off force that is configured to break the magnetic connection between the first or second magnetic coupling features.

Example 15

The sphincter sizing instrument of any one or more of Examples 1 through 14, wherein the predetermined pull-off force is the same through a range of sizes of the loop which enable the first and second magnetic coupling features to form the magnetic connection at a range of different angles.

Example 16

A sphincter sizing instrument comprising: (a) a body that defines a lumen, wherein the body includes opposing proximal and distal ends, wherein the distal end includes a first magnetic coupling feature; and (b) a shaft that longitudinally translates through the lumen relative to the body, wherein the shaft includes: (1) opposing proximal and distal ends, (2) a coupler coupled with the distal end, wherein the coupler includes a second magnetic coupling feature configured to attract and couple with the first magnetic coupling feature to form a magnetic connection, wherein the magnetic connection is configured to provide a predetermined radial compression during sizing measurement to define a resting sphincter state.

Example 17

The sphincter sizing instrument of Example 16, wherein the magnetic connection between the first and second magnetic coupling features have a predetermined pull-off force that is configured to break the magnetic connection between the first or second magnetic coupling features.

Example 18

The sphincter sizing instrument of Example 17, wherein the proximal end of the shaft is configured to be moved relative to the distal end of the body to reduce an area of a loop defined by the shaft, wherein the predetermined pull-off force is the same through a range of sizes of the loop which enable the first and second magnetic coupling features to form the magnetic connection at a range of different angles.

Example 19

The sphincter sizing instrument of any one or more of Examples 16 through 18, wherein the predetermined radial compression is selectable by a user using a selection tool, wherein the selection tool includes a predetermined range of acceptable predetermined radial compression values, wherein selections outside of the predetermined range of acceptable predetermined radial compression values are configured to be prevented or produce a warning.

Example 20

A sphincter sizing instrument comprising: (a) a biocompatible cover, (b) a body comprising a plurality of layered flexible bistable spring bands that are disposed within the biocompatible cover, wherein the body has a bistable bias between a straight configuration and a curved configuration, wherein in the curved configuration the plurality of layered flexible bistable spring bands have a predetermined radial compression value, wherein the body includes indicator markings configured to indicate the size of the esophagus.

Example 21

A sphincter sizing instrument comprising: (a) a handle assembly, wherein the handle assembly comprises: (i) a handle body, and (ii) a plunger portion slidably coupled with the handle body; (b) a shaft assembly extending distally from the handle assembly, wherein the shaft assembly comprises: (i) an external sheath fixed to the handle body, and (ii) an interior shaft coupled to the plunger portion, wherein the interior shaft is slidable relative to the external sheath; (c) an end effector configured to encompass a bodily lumen, wherein the end effector comprises: (i) a flexible member comprising a distal tip, wherein the flexible member extends distally from the interior shaft, (ii) a first mechanical coupling feature fixed to the distal tip of the flexible member, (iii) a first magnetic coupling feature fixed to the distal tip of the flexible member, (iv) a second magnetic coupling feature fixed to the external sheath, wherein the first and second magnetic coupling features are configured to be magnetically attracted to each other to define an adjustable loop; and (v) a second mechanical coupling feature fixed to the external sheath, wherein the first and second mechanical coupling features are configured to selectively lock with each other; (d) an auto-tensioning feature configured to bias the plunger portion proximally relative to the handle body.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A sphincter sizing instrument comprising:
    (a) a body that defines a lumen, wherein the body includes opposing proximal and distal ends, wherein the distal end includes:
        (1) a first magnetic coupling feature, and
        (2) a first mechanical coupling feature; and
    (b) a shaft configured to longitudinally translate through the lumen relative to the body, wherein the shaft includes:
        (1) opposing proximal and distal ends, and
        (2) a coupler coupled with the distal end of the shaft, wherein the coupler includes:
            (A) a second magnetic coupling feature configured to attract the first magnetic coupling feature to form a magnetic connection, and
            (B) a second mechanical coupling feature disposed at a distal most tip of the coupler, wherein the first magnetic coupling feature is configured to rotate the second mechanical coupling feature from a first unlocked position to a second locked position to allow the second mechanical coupling feature to couple with the first mechanical coupling feature to selectively prevent the first and second magnetic coupling features from disengaging as the shaft is proximally moved through the lumen relative to the body.

2. The sphincter sizing instrument of claim 1, wherein the first magnetic coupling feature is configured to oppose the second magnetic coupling feature of the coupler.

3. The sphincter sizing instrument of claim 1, wherein the first and second mechanical coupling features are secured together under a predetermined loading in the second locked position.

4. The sphincter sizing instrument of claim 1, wherein the magnetic connection is rotationally encoded to allow the second mechanical coupling feature to rotationally align with the first mechanical coupling feature in the second locked position to measure the outer diameter of the sphincter.

5. The sphincter sizing instrument of claim 1, wherein the magnetic connection is rotationally encoded to create a correlated magnetic field such that the first and second mechanical coupling features self-align and couple together in a particular rotational orientation.

6. The sphincter sizing instrument of claim 5, wherein the correlated magnetic field is configured to both attract the coupler to the distal end of the body such that the first and second mechanical coupling features are adjacent one another in the first unlocked position and subsequently rotate the second mechanical coupling feature to positively engage the first mechanical coupling feature in the second locked position.

7. The sphincter sizing instrument of claim 1, wherein the first magnetic coupling feature includes at least first and second spaced magnets, wherein the first magnet has a first polarity and the second magnet has a second polarity, wherein the second magnetic coupling feature includes at least third and fourth spaced magnets, wherein the third magnet has the second polarity and the fourth magnet has the first polarity, wherein alignment of the first and second magnetic coupling features causes the first and third magnets to couple together and the second and fourth magnets to couple together.

8. The sphincter sizing instrument of claim 7, wherein alignment of the first and second magnetic coupling features causes the first and fourth magnets to repel one another, and the second and third magnets to repel one another.

9. The sphincter sizing instrument of claim 1, wherein the first magnetic coupling feature includes at least first, second, and third spaced magnets, wherein the first magnet has a first polarity, the second magnet has a second polarity, and the third magnet has the first polarity, wherein the second magnetic coupling feature includes at least fourth, fifth, and sixth spaced magnets, wherein the fourth magnet has the second polarity, the fifth magnet has the first polarity, and the sixth magnet has the second polarity, wherein alignment of the first and second magnetic coupling features causes the first and fourth magnets to couple together, the second and fifth magnets to couple together, and the third and sixth magnets to couple together.

10. The sphincter sizing instrument of claim 1, wherein the magnetic connection is configured to provide a predetermined radial compression during sizing measurement to define a resting sphincter state.

11. A sphincter sizing instrument comprising:
(a) a body that defines a lumen, wherein the body includes opposing proximal and distal ends, wherein the distal end includes:
  (1) a first magnetic coupling feature, and
  (2) a first mechanical coupling feature; and
(b) a shaft that extends in a longitudinal direction and is configured to longitudinally translate through the lumen relative to the body, wherein the shaft includes:
  (1) opposing proximal and distal ends, and
  (2) a coupler coupled with the distal end of the shaft, wherein the coupler includes:
    (A) a second magnetic coupling feature configured to initially attract the first magnetic coupling feature, wherein the first and second magnetic coupling features are rotationally encoded, and
    (B) a second mechanical coupling feature disposed at the distal end of the shaft, wherein the first magnetic coupling feature is configured to rotate the second mechanical coupling feature from a first unlocked position to a second locked position to allow the second mechanical coupling feature to couple with the first mechanical coupling feature to selectively prevent the first and second magnetic coupling features from disengaging as the shaft is proximally moved through the lumen relative to the body.

12. The sphincter sizing instrument of claim 1, further comprising a handle assembly extending proximally from the body and configured to be gripped by a user, wherein the handle assembly includes a plurality of indicator markings configured to correspond to different sizes of the sphincter.

13. A sphincter sizing instrument comprising:
(a) a body that defines a lumen, wherein the body includes opposing proximal and distal ends, wherein the distal end includes:
  (1) a first magnetic coupling feature, and
  (2) a first mechanical coupling feature; and
(b) a shaft configured to longitudinally translate through the lumen relative to the body, wherein the shaft includes:
  (1) opposing proximal and distal ends, and
  (2) a coupler coupled with the distal end of the shaft, wherein the coupler includes:
    (A) a second mechanical coupling feature, and
    (B) a second magnetic coupling feature configured to attract the first magnetic coupling feature in a first unlocked position where the first and second mechanical coupling features are adjacent one another, wherein the first and second magnetic coupling features are rotationally encoded and configured to subsequently rotate the second mechanical coupling feature from the first unlocked position to a second locked position where the first and second mechanical coupling features are locked together as the shaft is proximally moved through the lumen relative to the body to allow for measurement of an outer diameter of a sphincter.

14. The sphincter sizing instrument of claim 1, wherein the first mechanical coupling feature includes a first projection that extends proximally, wherein the second mechanical coupling feature includes a second projection that extends distally when coupled with the first projection of the first mechanical coupling feature.

15. The sphincter sizing instrument of claim 14, wherein the first projection extends from a first neck, wherein the second projection extend from a second neck, wherein the first projection is configured to positively engage the second projection to form the mechanical connection.

16. The sphincter sizing instrument of claim 11, wherein each of the first and second magnetic coupling features include at least first and second magnets.

17. The sphincter sizing instrument of claim 16, wherein the first and second magnets of the second mechanical coupling feature are configured to subsequently couple with the first and second magnets of the first mechanical coupling feature after being rotated by the first and second magnets of the first magnetic coupling feature selectively prevent the first and second magnetic coupling features from disengaging as the shaft is proximally moved through the lumen relative to the body.

18. The sphincter sizing instrument of claim 11, wherein an exposed portion of the first magnet of the second magnetic coupling feature has a first polarity, wherein an exposed portion of the first magnet of the second magnetic coupling feature has a second polarity that is opposite the first polarity.

19. The sphincter sizing instrument of claim 13, wherein the first and second mechanical coupling features are not in locking engagement in the first unlocked position.

20. The sphincter sizing instrument of claim 14, wherein the body defines a longitudinal axis, wherein the shaft is configured to extend along the longitudinal axis, wherein the first and second projections extend along the longitudinal axis.

* * * * *